US009970047B2

(12) United States Patent
Heartlein et al.

(10) Patent No.: US 9,970,047 B2
(45) Date of Patent: May 15, 2018

(54) QUANTITATIVE ASSESSMENT FOR CAP EFFICIENCY OF MESSENGER RNA

(71) Applicant: TRANSLATE BIO, INC., Cambridge, MA (US)

(72) Inventors: Michael Heartlein, Boxborough, MA (US); Frank DeRosa, Cambridge, MA (US); Anusha Dias, Cambridge, MA (US)

(73) Assignee: TRANSLATE BIO, INC., Cambridge, MA (US)

( * ) Notice: Subject to any disclaimer, the term of this patent is extended or adjusted under 35 U.S.C. 154(b) by 52 days.

(21) Appl. No.: 14/775,846

(22) PCT Filed: Mar. 14, 2014

(86) PCT No.: PCT/US2014/027587
§ 371 (c)(1),
(2) Date: Sep. 14, 2015

(87) PCT Pub. No.: WO2014/152659
PCT Pub. Date: Sep. 25, 2014

(65) Prior Publication Data
US 2016/0032356 A1    Feb. 4, 2016

Related U.S. Application Data

(60) Provisional application No. 61/784,337, filed on Mar. 14, 2013.

(51) Int. Cl.
*C12Q 1/68*    (2018.01)
*C07K 14/50*    (2006.01)
*C12N 9/00*    (2006.01)
*C07K 14/505*    (2006.01)
*C12N 9/02*    (2006.01)

(52) U.S. Cl.
CPC .............. *C12Q 1/68* (2013.01); *C07K 14/505* (2013.01); *C12N 9/0069* (2013.01); *C12Q 1/6823* (2013.01); *C12Y 113/12007* (2013.01)

(58) Field of Classification Search
None
See application file for complete search history.

(56) References Cited

U.S. PATENT DOCUMENTS

| | | |
|---|---|---|
| 2010/0035249 A1 | 2/2010 | Hayashizaki et al. |
| 2012/0251618 A1 | 10/2012 | Schrum et al. |
| 2016/0002705 A1 | 1/2016 | Heartlein et al. |

FOREIGN PATENT DOCUMENTS

WO    2017/149139 A1    9/2017

OTHER PUBLICATIONS

Albers et al., Analysis of mRNA 5'-Terminal Cap Structures and Internal N6 -Methyladenosine by Reversed-Phase High-Performance Liquid Chromatography; Analytical Biochemistry, vol. 113, pp. 118-123, 1981.*
Galipon, J. et al., Stress-induced 1 ncRNAs evade nuclear degradation and enter the translational machinery, Genes to Cells, 18(5):353-368 (2013).
Grudzien, E. et al., Novel cap analogs for in vitro sythesis of mRNAs with high translational efficiency, RNA, 10(9):479-1487 (2007).
International Search Report for PCT/US2014/027587, 6 pages (dated Jul. 24, 2014).
International Search Report for PCT/US2014/027602, 6 pages (dated Jul. 28, 2014).
Jemielity, J. et al., Novel "anti-reverse" cap analogs with superior translational properties, Cold Spring Harbor Laboratory Press, 9(9):1108-1122 (2003).
Kore, A. and Charles, I., Synthesis and evaluation of 2'-O-allyl substituted dinucleotide cap analog for mRNA translation, Bioorganics & Medicinal Chemistry, 18:8061-8065 (2010).
Kore, A. and Shanmugasundaram, M., Synthesis and biological evaluation of trimethyl-substituted cap analogs, Bioorganic & Medicinal Chemistry, 18:880-884 (2008).
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
Nojima, T. et al., The Interaction between Cap-binding Complex and RNA Export Factor is Required for Intronless mRNA Export, Journal of Biological Chemistry, 282(21):15645-15651 (2007).
Otsuka, Y. et al., Identification of a Cytoplasmic Complex That Adds a Cap onto 5'-Monophosphate RNA, Molecular and Cellular Biology, 29(8):2155-2167 (2009).
Tcherepanova, I. et al., Ectopic expression of a truncated CD40L protein from synthetic post-transcriptionally capped RNA in dendritic cells induces high levels of IL-12 secretion, BMC Molecular Biology, 9(1):pp. 1-13 (2008).
Theus, S. and Liarakos, C., A Simple Assay for Determining the Capping Efficiencies of RNA Polymerases Used for In Vitro Transcription, BioChromatography, 9(5):610-614 (1990).
Written Opinion for PCT/US2014/027587, 5 pages (dated Jul. 24, 2014).
Written Opinion for PCT/US2014/027602, 7 pages (dated Jul. 28, 2014).

* cited by examiner

*Primary Examiner* — Addison D Ault
(74) *Attorney, Agent, or Firm* — Fangli Chen; Proskauer Rose LLP

(57) ABSTRACT

The present invention provides, among other things, methods of quantitating mRNA capping efficiency, particularly for mRNA synthesized in vitro. In some embodiments, the methods comprise chromatographic methods of quantifying capping efficiency and methylation status of the caps.

15 Claims, 3 Drawing Sheets

A.

B.

C.

QUANTITATIVE ASSESSMENT FOR CAP EFFICIENCY OF MESSENGER RNA

CROSS-REFERENCE TO RELATED APPLICATIONS

This application is the U.S. National Stage entry from International Application No. PCT/US2014/027587, filed Mar. 14, 2014, which claims priority to U.S. provisional patent application Ser. No. 61/784,337, filed Mar. 14, 2013, the disclosures of both of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Jan. 18, 2018, is named MRT-1106-2US2_SL.txt and is 9,304 bytes in size.

BACKGROUND

Messenger RNA ("mRNA") therapy is becoming an increasingly important approach for the treatment of a variety of diseases. Effective mRNA therapy requires effective delivery of the mRNA to the patient and efficient production of the protein encoded by the mRNA within the patient's body. To optimize mRNA delivery and protein production in vivo, a proper cap are typically required at the 5' end of the construct, which protects the mRNA from degradation and facilitates successful protein translation. Therefore, accurate characterization of the capping efficiency is particularly important for determining the quality of mRNA for therapeutic applications.

SUMMARY OF THE INVENTION

The present invention provides improved methods for accurately and quantitatively determining the capping efficiency of mRNA, in particular, mRNA synthesized in vitro. As discussed above, proper capping is important for successful protein production in vivo. However, prior to the present invention, most cap assays are qualitative, which is not sufficient for assessing the quality of an mRNA based therapeutic product and related safety and efficacy for in vivo use. In fact, prior to the present invention, there is no method available that allows quantification of capping efficiency without permanent alterations of the mRNAs in a sample.

As described in detail below, the present invention is, in part, based on generation and quantification of capped and uncapped fragments by chromatography. Thus, the present invention provides a simple, reliable and efficient quantitative approach for assessing mRNA capping efficiency. The present invention is particularly useful for quality control during mRNA manufacture and for characterization of mRNA as an active pharmaceutical ingredient (API) in final therapeutic products.

In one aspect, the present invention provides methods of quantifying mRNA capping efficiency, comprising steps of: (1) providing an mRNA sample comprising capped mRNA and uncapped mRNA; (2) contacting the mRNA sample with a DNA oligonucleotide complimentary to a sequence in the 5' untranslated region of the mRNA adjacent to the cap or uncapped penultimate base of mRNA under conditions that permit the DNA oligonucleotide anneal to the sequence; (3) providing one or more nucleases that selectively degrade DNA/RNA hybrid and/or unannealed mRNA, resulting in capped and uncapped fragments; (4) separating the capped and uncapped fragments by chromatography; and (5) determining relative amount of the capped and uncapped fragments, thereby quantifying mRNA capping efficiency.

In some embodiments, inventive methods of the present invention can be used to quantify a cap having a structure of formula I:

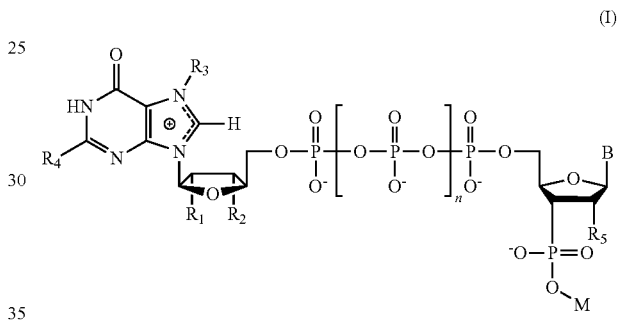

wherein,
B is a nucleobase;
$R_1$ is selected from a halogen, OH, and $OCH_3$;
$R_2$ is selected from H, OH, and $OCH_3$;
$R_3$ is $CH_3$, $CH_2CH_3$, $CH_2CH_2CH_3$ or void;
$R_4$ is $NH_2$;
$R_5$ is selected from OH, $OCH_3$ and a halogen;
n is 1, 2, or 3; and
M is a nucleotide of the mRNA.
In some embodiments, the nucleobase is guanine.
In some embodiments, inventive methods of the present invention can be used to quantify a $m^7G$ cap with a structure of formula II or an unmethylated cap with a structure of formula III.

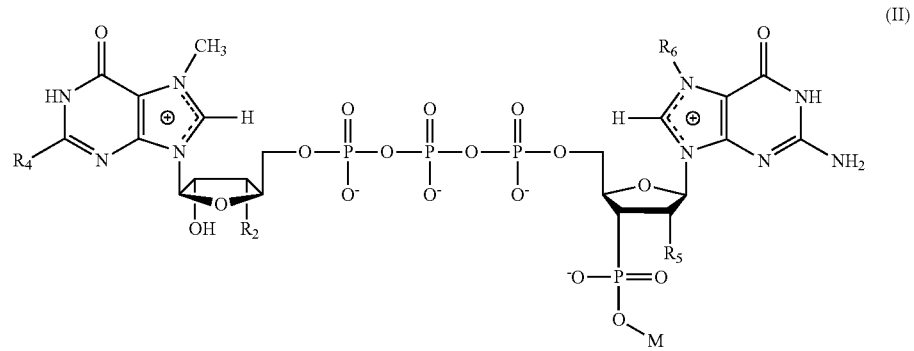

wherein,
$R_2$ is H or $CH_3$;
$R_4$ is $NH_2$;
$R_5$ is OH or $OCH_3$;
$R_6$ is H or $CH_3$; and
M is a nucleotide of the mRNA.

In some embodiments, step (5) of inventive methods described herein comprises determining relative peak areas of the capped and uncapped fragments.

In some embodiments, inventive methods according to the present invention are used to quantify mRNA capping efficiency of an mRNA sample synthesized in vitro.

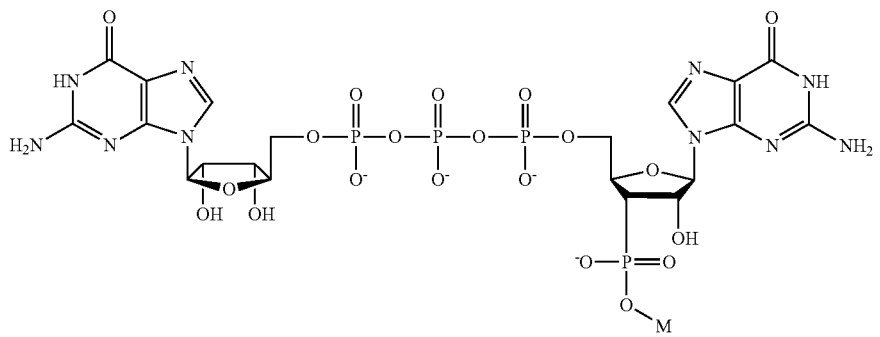

(III)

wherein M is a nucleotide of the mRNA.

In some embodiments, step (4) further separates methylated and unmethylated capped RNA. In some embodiments, the methylated cap comprises methylation at $R_3$ and/or $R_5$ position as shown in formula I. In some embodiments, an inventive method according to the present invention further includes a step of quantitatively determining methylation percentage of the capped RNA.

In some embodiments, a suitable DNA oligonucleotide is about 10-80 nucleotides in length (e.g., about 10-75, 10-70, 10-65, 10-60, 10-55, 10-50, 10-45, 10-40, 10-35, 10-30, 10-25, 10-20, or 10-15 nucleotides in length). In some embodiments, a suitable DNA oligonucleotide is or greater than about 10, 15, 20, 25, 30, 35, 40, 45, 50, 55, 60, 65, 70, 75, or 80 nucleotides in length. In some embodiments, a suitable DNA oligonucleotide is flanked on one or both sides by one or more RNA nucleotides (e.g., by 1, 2, 3, 4, 5, or more RNA nucleotides).

In some embodiments, a suitable DNA oligonucleotide is complimentary to a sequence in the 5' untranslated region of the mRNA within 1, 2, 3, 4, or 5 bases from the cap or uncapped penultimate base of mRNA.

In some embodiments, the one or more nucleases that selectively degrade DNA/RNA hybrid and/or unannealed RNA comprise RNase H. In some embodiments, the one or more nucleases that selectively degrade DNA/RNA hybrid and/or unannealed RNA comprise a nuclease that generates blunt-ended capped and uncapped fragments. In some embodiments, the one or more nucleases comprise nuclease S1 and/or RNAse H, or another 5' exonuclease.

In some embodiments, the capped and uncapped fragments from step (3) comprise no more than 5 bases (e.g., no more than 4, 3, 2, or 1) of the mRNA. In some embodiments, the capped and uncapped fragments from step (3) comprise no more than 2 bases of the mRNA.

In some embodiments, step (4) of inventive methods described herein comprises a step of applying the capped and uncapped fragments to a chromatographic column. In some embodiments, a suitable chromatographic column is selected from the group consisting of an anion-exchange HPLC column, a cation-exchange HPLC column, a reverse phase HPLC column, a hydrophobic interaction column, an ultra-performance liquid chromatography column, or a size exclusion column.

Among other things, the present invention further provides compositions and kits for performing inventive methods described herein. In some embodiments, the present invention provides a kit of quantifying mRNA capping efficiency, containing one or more of: (1) a DNA oligonucleotide complimentary to a sequence in the 5' untranslated region of an mRNA to be quantified adjacent to the cap or uncapped penultimate base of mRNA; (2) one or more reagents for annealing between DNA and RNA; (3) one or more nucleases (e.g., RNAse H and/or nuclease S1) that selectively degrade DNA/RNA hybrid and/or unannealed mRNA; and (4) one or more reagents for performing chromatography (e.g., a chromatographic column).

In yet another aspect, the present invention provides methods of manufacturing mRNA comprising a step of quantifying mRNA capping efficiency according to inventive methods described herein. In some embodiments, manufacturing methods according to the present invention contain a step of adjusting a manufacturing condition based on the result from quantifying mRNA capping efficiency. In some embodiments, the quantifying step is conducted before releasing an mRNA lot.

Among other things, the present invention further provides mRNA manufactured according to methods described herein.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes and are in no way limiting.

DEFINITIONS

Figure 1:
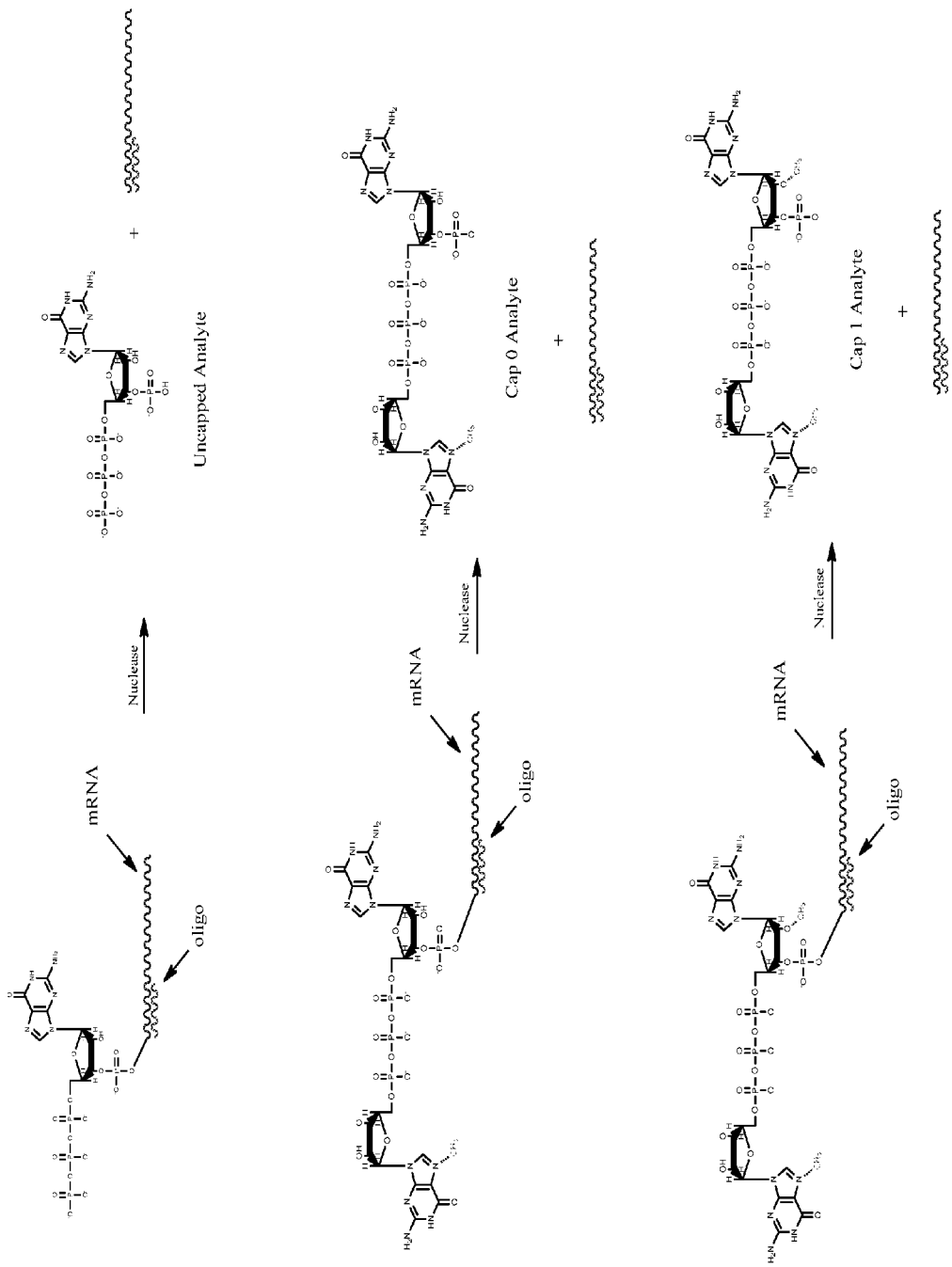
FIG. 1 depicts an exemplary embodiment comprising enzymatic manipulation of mRNA prior to chromatographic separation. A DNA oligonucleotide primer is used to anneal the mRNA adjacent to Cap0 or Cap1 structures, if present. A nuclease is provided to digest the RNA in the DNA:RNA hybrid, thereby producing a capped or uncapped analyte.

In order for the present invention to be more readily understood, certain terms are first defined. Additional definitions for the following terms and other terms are set forth throughout the specification.

Affinity: As is known in the art, "affinity" is a measure of the tightness with which a particular ligand binds to (e.g., associates non-covalently with) and/or the rate or frequency with which it dissociates from, its partner. As is known in the art, any of a variety of technologies can be utilized to determine affinity. In many embodiments, affinity represents a measure of specific binding.

Anneal or hybridization: As used herein, the terms "anneal," "hybridization," and grammatical equivalent, refers to the formation of complexes (also called duplexes or hybrids) between nucleotide sequences which are sufficiently complementary to form complexes via Watson-Crick base pairing or non-canonical base pairing. It will be appreciated that annealing or hybridizing sequences need not have perfect complementary to provide stable hybrids. In many situations, stable hybrids will form where fewer than about 10% of the bases are mismatches. Accordingly, as used herein, the term "complementary" refers to a nucleic acid molecule that forms a stable duplex with its complement under particular conditions, generally where there is about 90% or greater homology (e.g., about 95% or greater, about 98% or greater, or about 99% or greater homology). Those skilled in the art understand how to estimate and adjust the stringency of hybridization conditions such that sequences that have at least a desired level of complementarity will stably hybridize, while those having lower complementarity will not. For examples of hybridization conditions and parameters, see, for example, Sambrook et al., *"Molecular Cloning: A Laboratory Manual"*, 1989, Second Edition, Cold Spring Harbor Press: Plainview, N.Y. and Ausubel, *"Current Protocols in Molecular Biology"*, 1994, John Wiley & Sons: Secaucus, N.J. Complementarity between two nucleic acid molecules is said to be "complete", "total" or "perfect" if all the nucleic acid's bases are matched, and is said to be "partial" otherwise.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Chromatography: As used herein, the term "chromatography" refers to a technique for separation of mixtures. Typically, the mixture is dissolved in a fluid called the "mobile phase," which carries it through a structure holding another material called the "stationary phase." Column chromatography is a separation technique in which the stationary bed is within a tube, i.e., a column.

Compound and Agent: The terms "compound" and "agent" are used herein interchangeably. They refer to any naturally occurring or non-naturally occurring (i.e., synthetic or recombinant) molecule, such as a biological macromolecule (e.g., nucleic acid, polypeptide or protein), organic or inorganic molecule, or an extract made from biological materials such as bacteria, plants, fungi, or animal (particularly mammalian, including human) cells or tissues. The compound may be a single molecule or a mixture or complex of at least two molecules.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Kit: As used herein, the term "kit" refers to any delivery system for delivering materials. Such delivery systems may include systems that allow for the storage, transport, or delivery of various diagnostic or therapeutic reagents (e.g., oligonucleotides, antibodies, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a sub-portion of the total kit components. The containers may be delivered to the intended recipient together or separately. For example, a first container may contain an enzyme for use in an assay, while a second container contains oligonucleotides. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components in a single container (e.g., in a single box housing each of the desired components). The term "kit" includes both fragmented and combined kits.

Nucleoside: The term "nucleoside" or "nucleobase", as used herein, refers to adenine ("A"), guanine ("G"), cytosine ("C"), uracil ("U"), thymine ("T") and analogs thereof linked to a carbohydrate, for example D-ribose (in RNA) or 2'-deoxy-D-ribose (in DNA), through an N-glycosidic bond between the anomeric carbon of the carbohydrate (1'-carbon atom of the carbohydrate) and the nucleobase. When the nucleobase is purine, e.g., A or G, the ribose sugar is generally attached to the N9-position of the heterocyclic ring of the purine. When the nucleobase is pyrimidine, e.g., C, T or U, the sugar is generally attached to the N1-position of the heterocyclic ring. The carbohydrate may be substituted or unsubstituted. Substituted ribose sugars include, but are not limited to, those in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Ribose examples include ribose, 2'-deoxyribose, 2',3'-dideoxyribose, 2'-haloribose, 2'-fluororibose, 2'-chlororibose, and 2'-alkylribose, e.g., 2'-O-methyl, 4'-alpha-anomeric nucleotides, 1'-alpha-anomeric nucleotides (Asseline et al., NUCL. ACIDS RES., 19:4067-74 [1991]), 2'-4'- and 3'-4'-linked and other "locked" or "LNA," bicyclic sugar modifications (WO 98/22489; WO 98/39352; WO 99/14226).

Nucleotide: The term "nucleotide" as used herein means a nucleoside in a phosphorylated form (a phosphate ester of a nucleoside), as a monomer unit or within a polynucleotide polymer. "Nucleotide 5'-triphosphate" refers to a nucleotide with a triphosphate ester group at the 5' position, sometimes denoted as "NTP", or "dNTP" and "ddNTP" to particularly point out the structural features of the ribose sugar. The triphosphate ester group may include sulfur substitutions for the various oxygen moieties, e.g., alpha-thio-nucleotide 5'-triphosphates. Nucleotides can exist in the mono-, di-, or tri-phosphorylated forms. The carbon atoms of the ribose present in nucleotides are designated with a prime character (') to distinguish them from the backbone numbering in the bases. For a review of polynucleotide and nucleic acid chemistry see Shabarova, Z. and Bogdanov, A. Advanced Organic Chemistry of Nucleic Acids, VCH, New York, 1994.

Nucleic acid: The terms "nucleic acid", "nucleic acid molecule", "polynucleotide" or "oligonucleotide" may be used herein interchangeably. They refer to polymers of nucleotide monomers or analogs thereof, such as deoxyribonucleic acid (DNA) and ribonucleic acid (RNA) and combinations thereof. The nucleotides may be genomic, synthetic or semi-synthetic in origin. Unless otherwise stated, the terms encompass nucleic acid-like structures with synthetic backbones, as well as amplification products. As will be appreciated by one skilled in the art, the length of these polymers (i.e., the number of nucleotides it contains) can vary widely, often depending on their intended function or use. Polynucleotides can be linear, branched linear, or circular molecules. Polynucleotides also have associated counter ions, such as $H^+$, $NH_4^+$, trialkylammonium, $Mg^+$, $Na^+$ and the like. A polynucleotide may be composed entirely of deoxyribonucleotides, entirely of ribonucleotides, or chimeric mixtures thereof. Polynucleotides may be composed of internucleotide nucleobase and sugar analogs.

In some embodiments, the term "oligonucleotide" is used herein to denote a polynucleotide that comprises between about 5 and about 150 nucleotides, e.g., between about 10 and about 100 nucleotides, between about 15 and about 75 nucleotides, or between about 15 and about 50 nucleotides. Throughout the specification, whenever an oligonucleotide is represented by a sequence of letters (chosen, for example, from the four base letters: A, C, G, and T, which denote adenosine, cytidine, guanosine, and thymidine, respectively), the nucleotides are presented in the 5' to 3' order from the left to the right. A "polynucleotide sequence" refers to the sequence of nucleotide monomers along the polymer. Unless denoted otherwise, whenever a polynucleotide sequence is represented, it will be understood that the nucleotides are in 5' to 3' orientation from left to right.

Nucleic acids, polynucleotides and oligonucleotides may be comprised of standard nucleotide bases or substituted with nucleotide isoform analogs, including, but not limited to iso-C and iso-G bases, which may hybridize more or less permissibly than standard bases, and which will preferentially hybridize with complementary isoform analog bases. Many such isoform bases are described, for example, by Benner et al., (1987) Cold Spring Harb. Symp. Quant. Biol. 52, 53-63. Analogs of naturally occurring nucleotide monomers include, for example, 7-deazaadenine, 7-deazaguanine, 7-deaza-8-azaguanine, 7-deaza-8-azaadenine, 7-methylguanine, inosine, nebularine, nitropyrrole (Bergstrom, J. Amer. Chem. Soc., 117:1201-1209 [1995]), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, 0-6-methylguanine, N-6-methyladenine, O-4-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman (1989) in Practical Handbook of Biochemistry and Molecular Biology, pp. 385-394, CRC Press, Boca Raton, Fla.).

The term "3'" refers to a region or position in a polynucleotide or oligonucleotide 3' (i.e., downstream) from another region or position in the same polynucleotide or oligonucleotide. The term "5'" refers to a region or position in a polynucleotide or oligonucleotide 5' (i.e., upstream) from another region or position in the same polynucleotide or oligonucleotide. The terms "3' end" and "3' terminus", as used herein in reference to a nucleic acid molecule, refer to the end of the nucleic acid which contains a free hydroxyl group attached to the 3' carbon of the terminal pentose sugar. The term "5' end" and "5' terminus", as used herein in reference to a nucleic acid molecule, refers to the end of the nucleic acid molecule which contains a free hydroxyl or phosphate group attached to the 5' carbon of the terminal pentose sugar. In some embodiments of the invention, oligonucleotide primers comprise tracts of poly-adenosine at their 5' termini.

Target: As used herein, the term "target" refers to a molecule of interest.

DETAILED DESCRIPTION

The present invention provides, among other things, improved methods for quantifying mRNA capping efficiency. In some embodiments, the present invention provides a method of quantifying mRNA capping efficiency based on generating capped and uncapped fragments, separating the capped and uncapped fragments by chromatography, and determining relative amount of the capped and uncapped fragments. In some embodiments, the capped and uncapped fragments can be generated by contacting an mRNA sample with a DNA oligonucleotide complimentary to a sequence in the 5' untranslated region of the mRNA adjacent to the cap or uncapped penultimate base of mRNA under conditions that permit the DNA oligonucleotide to anneal to the sequence; and selectively degrading DNA/RNA hybrid and/or unannealed mRNA by one or more nucleases (e.g., nuclease S1, RNAse H, and/or other 5' exonuclease). In some embodiments, a chromatography-based method can further separate methylated and unmethylated capped mRNA and determine methylation state and percentage of the capped mRNA.

Various embodiments of the present invention are useful in quantitating capping efficiency during in vitro mRNA synthesis. Thus, the present invention provides an important quality control approach for manufacturing mRNA and, in particular, for assessing the safety, efficacy and commercially feasibility of mRNAs with therapeutic applications.

Various aspects of the invention are described in detail in the following sections. The use of sections is not meant to limit the invention. Each section can apply to any aspect of the invention. In this application, the use of "or" means "and/or" unless stated otherwise.

mRNA Capping and/or Methylation

Typically, eukaryotic mRNAs bear a "cap" structure at their 5'-termini, which plays an important role in translation. For example, the cap plays a pivotal role in mRNA metabolism, and is required to varying degrees for processing and maturation of an RNA transcript in the nucleus, transport of mRNA from the nucleus to the cytoplasm, mRNA stability, and efficient translation of the mRNA to protein. The 5' cap structure is involved in the initiation of protein synthesis of eukaryotic cellular and eukaryotic viral mRNAs and in mRNA processing and stability in vivo (see, e.g, Shatkin, A. J., CELL, 9: 645-653 (1976); Furuichi, et al., NATURE, 266: 235 (1977); FEDERATION OF EXPERIMENTAL BIOLOGISTS SOCIETY LETTER 96: 1-11 (1978); Sonenberg, N., PROG. NUC. ACID RES MOL BIOL, 35: 173-207 (1988)). Specific cap binding proteins exist that are components of the machinery required for initiation of translation of an mRNA (see, e.g., Shatkin, A. J., CELL, 40: 223-24 (1985); Sonenberg, N., PROG. NUC. ACID RES MOL BIOL, 35: 173-207 (1988)). The cap of mRNA is recognized by the translational initiation factor eIF4E (Gingras, et al., ANN. REV. BIOCHEM. 68: 913-963 (1999); Rhoads, R. E., J. BIOL. CHEM. 274: 30337-3040 (1999)). The 5' cap structure also provides resistance to 5'-exonuclease activity and its absence results in rapid degradation of the mRNA (see, e.g., Ross, J., MOL. BIOL. MED. 5: 1-14 (1988); Green, M. R. et al., CELL, 32: 681-694 (1983)). Since the primary transcripts of many eukaryotic cellular genes and eukaryotic viral genes require processing to remove intervening sequences (introns) within the coding regions of these transcripts, the benefit of the cap also extends to stabilization of such pre-mRNA.

In vitro, capped RNAs have been reported to be translated more efficiently than uncapped transcripts in a variety of in vitro translation systems, such as rabbit reticulocyte lysate or wheat germ translation systems (see, e.g., Shimotohno, K., et al., PROC. NATL. ACAD. SCI. USA, 74: 2734-2738 (1977); Paterson and Rosenberg, NATURE, 279: 692 (1979)). This effect is also believed to be due in part to protection of the RNA from exoribonucleases present in the in vitro translation system, as well as other factors.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription. A disadvantage of using $m^7G(5')ppp(5')G$, a pseudosymmetrical dinucleotide, is the propensity of the 3'-OH of either the G or $m^7G$ moiety to serve as the initiating nucleophile for transcriptional elongation. In other words, the presence of a 3'-OH on both the $m^7G$ and G moieties leads to up to half of the mRNAs incorporating caps in an improper orientation. This leads to the synthesis of two isomeric RNAs of the form $m^7G(5')pppG(pN)_n$ and $G(5')pppm^7G(pN)n$, in approximately equal proportions, depending upon the ionic conditions of the transcription reaction. Variations in the isomeric forms can adversely effect in vitro translation and are undesirable for a homogenous therapeutic product.

To date, the usual form of a synthetic dinucleotide cap used in in vitro translation experiments is the Anti-Reverse Cap Analog ("ARCA"), which is generally a modified cap analog in which the 2' or 3' OH group is replaced with —$OCH_3$. ARCA and triple-methylated cap analogs are incorporated in the forward orientation. Chemical modification of $m^7G$ at either the 2' or 3' OH group of the ribose ring results in the cap being incorporated solely in the forward orientation, even though the 2' OH group does not participate in the phosphodiester bond. (Jemielity, J. et al., "Novel 'anti-reverse' cap analogs with superior translational properties", RNA, 9: 1108-1122 (2003)). The selective procedure for methylation of guanosine at N7 and 3' O-methylation and 5' diphosphate synthesis has been established (Kore, A. and Parmar, G. NUCLEOSIDES, NUCLEOTIDES, AND NUCLEIC ACIDS, 25:337-340, (2006) and Kore, A. R., et al. NUCLEOSIDES, NUCLEOTIDES, AND NUCLEIC ACIDS 25(3): 307-14, (2006).

Transcription of RNA usually starts with a nucleoside triphosphate (usually a purine, A or G). In vitro transcription typically comprises a phage RNA polymerase such as T7, T3 or SP6, a DNA template containing a phage polymerase promoter, nucleotides (ATP, GTP, CTP and UTP) and a buffer containing magnesium salt. The synthesis of capped RNA includes the incorporation of a cap analog (e.g., $m^7GpppG$) in the transcription reaction, which in some embodiments is incorporated by the addition of recombinant guanylyl transferase. Excess $m^7GpppG$ to GTP (4:1) increases the opportunity that each transcript will have a 5' cap. Kits for capping of in vitro transcribed mRNAs are commercially available, including the mMESSAGE mMACHINE® kit (Ambion, Inc., Austin, Tex.). These kits will typically yield 80% capped RNA to 20% uncapped RNA, although total RNA yields are lower as GTP concentration becomes rate limiting as GTP is needed for the elongation of the transcript. However, currently there is no technology/method available that will allow quantification of capping efficiency without permanent alterations of the mRNAs in a sample.

Methods of estimating capping efficiency are known in the art. For example, the T7 RNA polymerase can be incubated with a cap dinucleotide, all four ribonucleotide triphosphates, [$\alpha$-$^{32}$P]GTP, and a short DNA template in which G is the first ribonucleotide specified after the promoter (see Grudzien, E. et al. "Novel cap analogs for in vitro synthesis of mRNA with high translation efficiency", RNA, 10: 1479-1487 (2004)). Any nucleotide on the 5' side of a G residue acquires a ³²P-labeled 3'-phosphate group after RNase T2 digestion by nearest-neighbor transfer. Anion exchange chromatography is then used to resolve labeled nucleoside 3'-monophosphates, resulting from internal positions in the RNA, from 5'-terminal products. 5'-terminal products are of two types. Uncapped RNAs yield labeled guanosine 5'-triphosphate 3'-monophosphate (p3Gp*; in which * indicates the labeled phosphate group). Capped RNAs yield various 5'-terminal structures, depending on the nature of the cap analog used (m⁷Gp3Gp* and Gp3 m⁷Gp* when the cap analog is m⁷Gp3G).

However, a major drawback of these methods is that the entire sample is rendered radioactive or otherwise destroyed, and thus cannot be used in subsequent therapeutic applications. Although in theory a separate quantification reaction could be run alongside a therapeutic synthesis reaction, such arrangements are inadequate. Simultaneous but separate samples are inherently variable due to intra-operator error and minute variations in reaction conditions. This is particularly true for quantifications using a standard curve, in which a value for a point on the standard curve on one given day may not be the same on the next day. To obtain accurate results in calculating capping efficiency, it is desirable to use a representative sample taken from the therapeutic synthesis reaction, a sample for which capping efficiency can be evaluated relative to controls and which is representative of the capping efficiency in the therapeutic synthesis reaction.

Thus, the present invention provides improved methods of directly quantitating mRNA capping efficiency in a sample (e.g., a representative aliquot sample from an in vitro synthesis reaction). Some embodiments of the invention comprise chromatographic methods of quantitating mRNA capping efficiency. These methods are based in part on the insights that the versatility of enzymatic manipulation can be used to increase the resolution of chromatographic separation of polynucleotides. (FIG. 1) Thus, by amplifying the power of chromatographic separation through enzymatic manipulation, embodiments of the invention increase the efficiency, quality and throughput of quantitation. For example, not only can the chromatographic methods described herein quantitate capping efficiency, they can also provide information on the modification of the cap (e.g., methylation status at particular cap positions). Thus, embodiments of the invention can simultaneously quantitate capping efficiency and the efficiency of cap modification (e.g., methylation efficiency). This quantification provides important characterization of an mRNA drug product that has significant impact on the protein production.

Chromatographic embodiments of the invention can be used to quantify any of the cap structure and cap analogs described herein, as well as various modifications within the caps. Particular embodiments utilize the natural biological activity of specific nucleases to provide quantitative information of capping efficiency and the efficiency of methylation of the cap guanine base (e.g., N-7 position). Additional embodiments can also simultaneously quantitate methylation of the 2'-O position of the ribose ring for the penultimate base (Cap1 structure, see FIG. 2). Embodiments of the invention may be used to quantify the capping efficiency of a wide variety of RNA species, including in vitro transcribed mRNA, isolated eukaryotic mRNA, and viral RNA.

Enzymatic manipulation is facilitated through the use of a DNA oligonucleotide complimentary to a sequence in the 5' untranslated region of the mRNA adjacent to the cap or uncapped penultimate base of mRNA. (FIG. 1) The DNA oligonucleotide is added to an mRNA sample comprising capped mRNA and uncapped mRNA under conditions that permit the DNA oligonucleotide to anneal to the specified sequence in the untranslated region. A nuclease is then provided, which selectively degrades DNA/RNA hybrid and/or unannealed mRNA, resulting in capped and uncapped 5' fragments. (FIG. 1) In some embodiments, at least a portion of the fragment is double-stranded. In some embodiments, the double-stranded portion is at least partially an RNA:RNA hybrid. In some embodiments, the double-stranded portion is at least partially an DNA:RNA hybrid. Fragments resulting from nuclease treatment may be blunt-ended or staggered. In some embodiments, the fragments are between 2-20 nucleotides (including a cap nucleotide if present); i.e. fragments resulting from nuclease treatment can be 20 nucleotides, 19 nucleotides, 18 nucleotides, 17 nucleotides, 16 nucleotides, 15 nucleotides, 14 nucleotides, 13 nucleotides, 12 nucleotides, 11 nucleotides, 10 nucleotides, 9 nucleotides, 8 nucleotides, 7 nucleotides, 6 nucleotides, 5 nucleotides, 4 nucleotides, 3 nucleotides or 2 nucleotides. In some embodiments, the capped and uncapped fragments comprise no more than 5 bases of the mRNA. In some embodiments, the capped and uncapped fragments comprise no more than 2 bases of the mRNA.

The capped and uncapped fragments are then resolved (i.e., separated from one another) by chromatography. The amount of capped and uncapped fragments can then be quantitated by standard quantitative chromatography techniques, for example HPLC peak integration.

Embodiments of the invention are not limited by the type or size of DNA oligonucleotide. In some embodiments, the oligonucleotide comprises between 10-80 nucleotides; e.g., 10 nucleotides, 15 nucleotides, 20 nucleotides, 25 nucleotides, 30 nucleotides, 35 nucleotides, 40 nucleotide, 45 nucleotides, 50 nucleotides or more. The size of the DNA oligonucleotide can be selected to generate a capped fragment (if present) of desired length. The DNA oligonucleotide may also be designed to hybridize to any region of the 5' untranslated region depending on where cleavage is desired; i.e., can be positioned within the 5' untranslated region to produce a capped fragment (if present) of any size. In particular, a suitably designed oligonucleotide comprising a small stretch of DNA bases (e.g. about 1, 2, 3, 4, 5, 6, 7, 8, 9, 10, 12, 14, 16, 18, or 20 nucleotides) flanked by RNA bases (e.g., 1-15) on each side (i.e., a "gapmer") can be annealed to the mRNA analyte. Designing such an oligonucleotide to bind to the complementary bases of the 5' untranslated region of the mRNA allows for select cleavage via DNA/RNA hybrid recognition of RNAse H. Similarly, a suitably designed oligonucleotide may comprise a small stretch of DNA bases (e.g., about 1, 2, 3, 4, 5, 6, 7, 8, 9, 10, 12, 14, 16, 18 or 20 nucleotides) flanked only at one end (e.g., the 5' or 3' end) by RNA bases (e.g., 1-15).

In preferred embodiments, the oligonucleotide is designed to bind directly adjacent to the cap and/or penultimate base of the mRNA construct, allowing for the resulting cleaved bases to consist of the initial two (or few) bases of the mRNA construct. Without wishing to be bound by any particular theory, it is thought desirable to produce small capped and uncapped fragments in order to improve the chromatography resolution; i.e., to improve the separation of capped and uncapped fragments and quantify relative amounts. Generally speaking, the smaller the fragment, the better the separation and quantification. In some embodiments, the first base of the DNA oligonucleotide binds at the penultimate base of the mRNA. In some embodiments, the first base of the DNA oligonucleotide binds adjacent to the penultimate base of the mRNA (i.e., at M of Formula 1). In some embodiments, the first base of the DNA oligonucleotide binds at least 2 nucleotides, at least 3 nucleotides, at least 4 nucleotides, at least 5 nucleotides, at least 6 nucleotides, at least 7 nucleotides, at least 8 nucleotides, at least 9 nucleotides or at least 10 nucleotides from the penultimate base of the mRNA.

Embodiments of the invention are not limited by the identity of the nuclease. Any nuclease capable of cleaving or digesting at least one strand of a DNA:RNA hybrid may be used. As mentioned above, multiple nucleases may be used in a single reaction to effect production of a capped fragment or produce both a capped fragment (if present) and blunt-end the capped fragment. In some embodiments, a suitable nuclease is RNase H or an enzyme with RNAse H-like biochemical activity. RNases H are a ubiquitous enzyme family that is divided into two distinct phylogenetic subtypes, Type 1 and Type 2, either of which may be used in particular embodiments. The RNases H are unified by the common ability to bind a single-stranded (ss) RNA that is hybridized to a complementary DNA single strand, and then degrade the RNA portion of the RNA:DNA hybrid. While the RNases H have been implicated in DNA replication and recombination, and repair, their physiological roles are not completely understood. In vitro, the enzymes will also bind double-stranded (ds) DNA, ssDNA, ssRNA, and dsRNA, albeit with lower affinities than they bind to RNA:DNA hybrids. Due to the ubiquity of the enzyme, there are several sequences for RNase H known in the literature, each of which vary somewhat in their amino acid sequences. U.S. Pat. No. 5,268,289 discloses a thermostable RNase H, as does U.S. Pat. No. 5,500,370. U.S. Pat. No. 6,376,661 discloses a human RNase H and compositions and uses thereof. U.S. Pat. No. 6,001,652 discloses a human type 2 RNase H. U.S. Pat. No. 6,071,734 discloses RNase H from HBV polymerase. All of these RNases H may be used in one more embodiments of the invention.

In some embodiments, a suitable nuclease is S1 nuclease. In some embodiments, multiple nucleases are used; for example RNase H and an S1 nuclease. Additional nucleases that may be utilized, either alone or in combination, in embodiments of the invention include Benzonase®, Nuclease P1, Phosphodiesterase II, RNase A, and RNase T1. Some embodiments further comprise addition of a single-stranded DNA nuclease to finally produce or modify the fragment. In some embodiments, it may be desired to heat the sample (e.g., to about 60° C.) or apply the sample to a heated chromatographic column in order to effectuate production of the capped fragments.

The nuclease-treated sample is then applied to a chromatographic column to separate capped from uncapped fragments. In addition to separating capped from uncapped fragment, chromatography can resolve and quantitate a methylated cap from an unmethylated guanine cap. In some embodiments, a methylated penultimate base (2'-O-methylated base) can be separated (resolved) and quantitated from a cap unmethylated at that position. Current chromatography protocols can differentiate as any combination of the species that may arise from the in vitro synthetic process. Various aspects of chromatographic embodiments are discussed in more detail below.

mRNA Caps

Inventive methods described herein are generally amenable to quantification of any type of mRNA cap. In some embodiments, the cap has a structure of formula I:

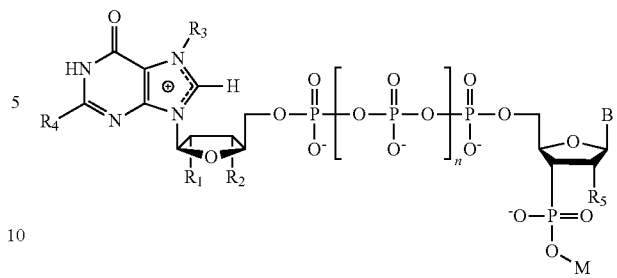

wherein B is a nucleobase, $R_1$ is selected from a halogen, OH, and $OCH_3$, $R_2$ is selected from H, OH, and $OCH_3$, $R_3$ is $CH_3$, $CH_2CH_3$, $CH_2CH_2CH_3$ or void, $R_4$ is $NH_2$, $R_5$ is selected from OH, $OCH_3$ and a halogen, n is 1, 2, or 3, and M is a nucleotide, i.e., the third base of mRNA. In particular embodiments, B is guanine, but can be any nucleobase. In some embodiments, the cap is $m^7G(5')ppp(5')G$ in which a 2'-O-methyl residue is present at the 2' OH group of the ribose ring of base 1 (i.e., at the $R_5$ position of Formula 1).

Cap analogs may be or comprise any modified "G" base (e.g., one or more modified guanine nucleotides). Suitable cap analogs include, but are not limited to, a chemical structures selected from the group consisting of $m^7GpppG$, $m^7GpppA$, $m^7GpppC$; unmethylated cap analogs (e.g., $GpppG$); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{7,2'd}GpppG$, $m^{7,3'Ome}GpppG$, $m^{7,3'd}GpppG$ and their tetraphosphate derivatives) (see, e.g., Jemielity, J. et al., "Novel 'anti-reverse' cap analogs with superior translational properties", RNA, 9: 1108-1122 (2003)).

In a preferred embodiment, the cap is a 7-methyl guanylate ("$m^7G$") linked via a triphosphate bridge to the 5'-end of the first transcribed nucleotide, resulting in $m^7G(5')ppp(5')N$, where N is any nucleoside. A preferred embodiment of a $m^7G$ cap utilized in embodiments of the invention is $m^7G(5')ppp(5')G$.

In some embodiments, mRNA is uncapped. (FIG. 2A) Uncapped mRNA may be present in a sample (i.e., as a result of incomplete capping in an in vitro transcription reaction) and/or may be used a control to quantitative the level of uncapped species in a sample. In some embodiments, the cap is a Cap0 structure. (FIG. 2B). Cap0 structures lack a 2'-O-methyl residue of the ribose attached to bases 1 and 2. In some embodiments, the cap is a Cap1 structure. (FIG. 2C) Cap1 structures have a 2'-O-methyl residue at base 1. In some embodiments, the cap is a Cap2 structure. Cap2 structures have a 2'-O-methyl residue attached to both bases 1 and 2.

A variety of $m^7G$ cap analogs are known in the art, many of which are commercially available. These include the $m^7GpppG$ described above, as well as the ARCA 3'-$OCH_3$ and 2'-$OCH_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Production of Capped mRNAs

Capped mRNAs suitable for the quantitative methods disclosed herein may be produced by any method known in the art.

In some embodiments, capped mRNA is produced by in vitro transcription, originally developed by Krieg and Melton (METHODS ENZYMOL., 1987, 155: 397-415) for the synthesis of RNA using an RNA phage polymerase. Typically these reactions include at least a phage RNA polymerase (T7, T3 or SP6), a DNA template containing a phage polymerase promoter, nucleotides (ATP, CTP, GTP and UTP), and a buffer containing a magnesium salt. RNA synthesis yields may be optimized by increasing nucleotide concentrations, adjusting magnesium concentrations and by including inorganic pyrophosphatase (U.S. Pat. No. 5,256,555; Gurevich, et al., ANAL. BIOCHEM. 195: 207-213 (1991); Sampson, J. R. and Uhlenbeck, O. C., PROC. NATL. ACAD. SCI. USA. 85, 1033-1037 (1988); Wyatt, J. R., et al., BIOTECHNIQUES, 11: 764-769 (1991)). Some embodiments utilize commercial kits for the large-scale synthesis of in vitro transcripts (e.g., MEGAscript®, Ambion). The RNA synthesized in these reactions is usually characterized by a 5' terminal nucleotide that has a triphosphate at the 5' position of the ribose. Typically, depending on the RNA polymerase and promoter combination used, this nucleotide is a guanosine, although it can be an adenosine (see e.g., Coleman, T. M., et al., NUCLEIC ACIDS RES., 32: e14 (2004)). In these reactions, all four nucleotides are typically included at equimolar concentrations and none of them is limiting.

Some embodiment of the invention are batch reactions—that is, all components are combined and then incubated at about 37° C. to promote the polymerization of the RNA until the reaction terminates. Typically, a batch reaction is used for convenience and to obtain as much RNA as needed from such reactions for their experiments. In some embodiments, a "fed-batch" system (see, e.g., JEFFREY A. KERN, BATCH AND FED-BATCH STRATEGIES FOR LARGE-SCALE PRODUCTION OF RNA BY IN VITRO TRANSACTION (University of Colorado) (1997)) is used to increase the efficiency of the in vitro transcription reaction. All components are combined, but then additional amounts of some of the reagents are added over time, such as the nucleotides and magnesium, to try to maintain constant reaction conditions. In addition, in some embodiments, the pH of the reaction may be held at 7.4 by monitoring it over time and adding KOH as needed.

To synthesize a capped RNA by in vitro transcription, a cap analog (e.g., N-7 methyl GppppG; i.e., m$^7$GpppG) is included in the transcription reaction. In some embodiments, the RNA polymerase will incorporate the cap analog as readily as any of the other nucleotides; that is, there is no bias for the cap analog. In some embodiments, the cap analog will be incorporated at the 5' terminus by the enzyme guanylyl transferase In some embodiments, the cap analog will be incorporated only at the 5' terminus because it does not have a 5' triphosphate. In some embodiments using a T7, T3 and SP6 RNA polymerase, the +1 nucleotide of their respective promoters is usually a G residue and if both GTP and m$^7$GpppG are present in equal concentrations in the transcription reaction, then they each have an equal chance of being incorporated at the +1 position. In some embodiments, m$^7$GpppG is present in these reactions at several-fold higher concentrations than the GTP to increase the chances that a transcript will have a 5' cap. In some embodiments, a mMESSAGE mMACHINE® kit (Cat. #1344, Ambion, Inc.) is used according to manufacturer's instructions, where it is recommended that the cap to GTP ratio be 4:1 (6 mM: 1.5 mM). In some embodiments, as the ratio of the cap analog to GTP increases in the reaction, the ratio of capped to uncapped RNA increases proportionally. Considerations of capping efficiency must be balanced with considerations of yield. Increasing the ratio of cap analog to GTP in the transcription reaction produces lower yields of total RNA because the concentration of GTP becomes limiting when holding the total concentration of cap and GTP constant. Thus, the final RNA yield is dependent on GTP concentration, which is necessary for the elongation of the transcript. The other nucleotides (ATP, CTP, UTP) are present in excess.

In particular embodiments, mRNA are synthesized by in vitro transcription from a plasmid DNA template encoding a gene of choice. In some embodiments, in vitro transcription includes addition of a 5' cap structure, Cap1 (FIG. 2C), which has a 2'-O-methyl residue at the 2' OH group of the ribose ring of base 1, by enzymatic conjugation of GTP via guanylyl transferase. In some embodiments, in vitro transcription includes addition of a 5' cap structure, Cap0 (FIG. 2B), which lacks the 2'-O-methyl residue, by enzymatic conjugation of GTP via guanylyl transferase. In some embodiments, in vitro transcription includes addition of a 5' cap of any of the cap structures disclosed herein by enzymatic conjugation of GTP via guanylyl transferase. In some embodiments, a 3' poly(A) tail of approximately 200 nucleotides in length (as determined by gel electrophoresis) was incorporated through the addition of ATP in conjunction with PolyA polymerase. In some embodiments, the poly(A) tail is approximately 100-250 nucleotides in length. In some embodiments, the poly(A) tail is about 50-300 nucleotides in length. In some embodiments, the in vitro transcription products include 5' and 3' untranslated regions.

Chromatographic Separation

Embodiments of the invention utilize chromatography to provide highly resolved (e.g. single base resolution) capped and uncapped fragments. Fragments can be efficiently resolved by thin-layer chromatography ("TLC") or high performance liquid chromatography ("HPLC"). In the context of the present invention, the term "HPLC" includes various HPLC methods as well as low or normal pressure liquid chromatography methods, which may be used to carry out some embodiments of the invention. In some embodiments, fragments may be resolved by one or more of size exclusion chromatography-high performance liquid chromatography (SEC-HPLC) and/or reverse phase-high performance liquid chromatography (RP-HPLC) (e.g., using columns of octadecyl (C18)-bonded silica, and carried out at an acidic pH with TFA as a counter-ion). In some embodiments of the invention, the major peak in the chromatogram is capped mRNA fragments. Parameters that may be altered or optimized to increase resolution include gradient conditions, organic modifier, counter ion, temperature, column pore size and particle size, solvent composition and flow rate.

The quantitative methods described herein can include one or more steps of ion exchange chromatography-HPLC (e.g., anion exchange-HPLC and/or cation exchange-HPLC). As will be known by those skilled in the art, ion exchangers (e.g., anion exchangers and/or cation exchangers) may be based on various materials with respect to the matrix as well as to the attached charged groups. For example, the following matrices may be used, in which the materials mentioned may be more or less crosslinked: agarose based (such as Sepharose™ CL-6B, Sepharose™ Fast Flow and Sepharose™ High Performance), cellulose based (such as DEAE Sephacel®), dextran based (such as SEPHADEX®), silica based and synthetic polymer based.

The ion exchange resin can be prepared according to known methods. Typically, an equilibration buffer, which allows the resin to bind its counter ions, can be passed through the ion exchange resin prior to loading the sample or composition comprising the polypeptide and one or more contaminants onto the resin. Conveniently, the equilibration buffer can be the same as the loading buffer, but this is not required. In an optional embodiment of the invention, the ion exchange resin can be regenerated with a regeneration buffer after elution of the polypeptide, such that the column can be re-used. Generally, the salt concentration and/or pH of the regeneration buffer can be such that substantially all contaminants and the polypeptide of interest are eluted from the ion exchange resin. Generally, the regeneration buffer has a very high salt concentration for eluting contaminants and fragments from the ion exchange resin.

Some embodiments of the invention include, for example, subjecting samples to anion exchange chromatography. High-resolution analysis of nucleotide fragment may be performed as described in Ausser, W. A., et al., "High-resolution analysis and purification of synthetic oligonucleotides with strong anion-exchange HPLC", BIOTECHNIQUES, 19: 136-139 (1995), incorporated herein by reference. For the anion exchange resin, the charged groups which are covalently attached to the matrix can be, for example, diethylaminoethyl (DEAE), quaternary aminoethyl (QAE), and/or quaternary ammonium (Q). In some embodiments, the anion exchange resin employed is a Q Sepharose column. The anion exchange chromatography can be performed, for example, using, e.g., Q Sepharose™ Fast Flow, Q Sepharose™ High Performance, Q Sepharose™ XL, Capto™ Q, DEAE, TOYOPEARL Gigacap® Q, Fractogel® TMAE (trimethylaminoethyl, a quarternary ammonia resin), Eshmuno™ Q, Nuvia™ Q, or UNOsphere™ Q. Other anion exchangers can be used within the scope of the invention, including but not limited to, quaternary amine resins or "Q-resins" (e.g., Capto™-Q, Q-Sepharose®, QAE Sephadex®); diethylaminoethane resins (e.g., DEAE-Trisacryl®, DEAE Sepharose®, benzoylated naphthoylated DEAE, diethylaminoethyl Sephacel®); Amberjet® resins; Amberlyst® resins; Amberlite® resins (e.g., Amberlite® IRA-67, Amberlite® strongly basic, Amberlite® weakly basic), cholestyramine resin, ProPac@ resins (e.g., ProPac@ SAX-10, ProPac@ WAX-10, ProPac® WCX-10); TSK-GEL® resins (e.g., TSKgel DEAE-NPR; TSKgel DEAE-5PW); and Acclaim® resins.

Typical mobile phases for anionic exchange chromatography include relatively polar solutions, such as water, acetonitrile, organic alcohols such as methanol, ethanol, and isopropanol, or solutions containing 2-(N-morpholino)-ethanesulfonic acid (MES). Thus, in certain embodiments, the mobile phase includes about 0%, 1%, 2%, 4%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, or about 100% polar solution. In certain embodiments, the mobile phase comprises between about 1% to about 100%, about 5% to about 95%, about 10% to about 90%, about 20% to about 80%, about 30% to about 70%, or about 40% to about 60% polar solution at any given time during the course of the separation.

In some embodiments, samples are subject to cation exchange chromatography, e.g., sulfopropyl (SP) cation exchange chromatography. In a typical embodiment, the cation exchange chromatography comprises sulfopropyl (SP) cation exchange chromatography, but other cation chromatography membranes or resins can be used, for example, a MUSTANG™ S membrane, an S-Sepharose™ resin, or a Blue Sepharose™ resin. The cation exchange chromatography can be performed at an optimized temperature to enhance target binding and/or decrease impurity binding.

In some embodiments, samples are subjected to hydrophobic interaction chromatography (HIC). Hydrophobic interaction chromatography utilizes the attraction of a given molecule for a polar or non-polar environment, and in terms of nucleic acids, this propensity is governed by the hydrophobicity or hydrophilicity of nucleotides and modifications thereon. Thus, nucleic acids are fractionated based upon their varying degrees of attraction to a hydrophobic matrix, typically an inert support with alkyl linker arms of 2-18 carbons in chain length. The stationary phase consists of small non-polar groups (butyl, octyl, or phenyl) attached to a hydrophilic polymer backbone (e.g., cross-linked Sepharose™, dextran, or agarose). In some embodiments, the hydrophobic interaction chromatography includes phenyl chromatography. In other embodiments, the hydrophobic interaction chromatography includes butyl chromatography or octyl chromatography.

In some embodiments, fragments are resolved by reverse phase-HPLC. Reversed phase HPLC consists of a non-polar stationary phase and a moderately polar mobile phase. In some embodiments, the stationary phase is a silica which has been treated with, for example, $RMe_2SiCl$, where R is a straight chain alkyl group such as $C_{18}H_{37}$ or $C_8H_{17}$. The retention time is therefore longer for molecules which are more non-polar in nature, allowing polar molecules to elute more readily. Retention time is increased by the addition of polar solvent to the mobile phase and decreased by the addition of more hydrophobic solvent. The characteristics of the specific RNA molecule as an analyte may play an important role in its retention characteristics. In general, an analyte having more non-polar functional groups (e.g., methyl groups) results in a longer retention time because it increases the molecule's hydrophobicity. Protocols for high resolution of RNA species using reverse phase-HPLC, which may be adapted for use in embodiments of the invention, are known in the art (see, e.g., U.S. pre-grant publication 2010/0048883; Gilar, M., "Analysis and purification of synthetic oligonucleotides by reversed-phase high-performance liquid chromatography with photodiode array and mass spectrometry detection", ANAL. BIOCHEM., 298: 196-206 (2001)).

Particular embodiments of the invention utilize combinations of the various chromatographic separations disclosed herein. For example, particular embodiments of the invention may utilize reverse-phase ion-pair chromatography, whereby separations are based on both hydrophobicity and on the number of anions associated with the molecule, which may be used to purify fragments in a single HPLC step. Matricies can be silica-based (e.g., Murray et al., ANAL. BIOCHEM., 218:177-184 (1994)). Non-porous, inert polymer resins may be used in particular embodiments (see, e.g., Huber, C. G., "High-resolution liquid chromatography of oligonucleotides on nonporous alkylated styrene-divinylbenzene copolymers", ANAL. BIOCHEM., 212: 351-358 (1993)). Other combinations may be equally effective and must be evaluated in terms of the size of the fragment and the modifications sought to be resolved.

In some embodiments, a capping efficiency profile and/or methylation profile may be determined by strong anion exchange chromatography using a HPLC system. In general, uncapped mRNA adsorbs onto the fixed positive charge of a strong anion exchange column and a gradient of increasing ionic strength using a mobile phase at a predetermined flow rate elutes capped species (the cap bearing a positive charge) from the column in proportion to the strength of their ionic interaction with the positively charged column. More negatively charged (more acidic) uncapped species elute later than less negatively charged (less acidic) capped species.

In certain embodiments, capped fragments are characterized by the methylation profile associated with the fragment. Typically, methylation profiles reflect and quantitate the efficiency of methylation of the cap guanine base (N-7 position). Additional embodiments can also simultaneously quantitate methylation of the 2'-O position of the ribose ring for the penultimate base (Cap1 structure). In some embodiments, a methylation profile may be determined by performing reverse phase-HPLC, alone or in combination with ion exchange chromatography. In some embodiments, a "methylation profile" refers to a set of values representing the amount of methylated capped fragment that elutes from a column at a point in time after addition to the column of a mobile phase. As described above, the retention time for methylated caps and penultimate nucleotides, which are more non-polar in nature, is increased relative to polar molecules, which elute more readily. Retention time may be increased by the addition of polar solvent to the mobile phase and decreased by the addition of more hydrophobic solvent.

In some embodiments, ultra performance liquid chromatography ("UPLC") is used to resolve capped and uncapped fragments, and optionally to provide additional quantitative information on methylation states. UPLC refers generally to HPLC techniques using resin particle sizes less than 2.5 μm, which provides a significant gain in efficiency even at increased flow rates and linear velocities. By using small particles, speed and peak capacity (number of peaks resolved per unit time) can be extended. Such techniques utilize chromatographic principles to run separations using columns packed with smaller particles and/or higher flow rates for increased speed, with superior resolution and sensitivity. (see, e.g., Swartz, M. E., "Ultra Performance Liquid Chromatography (UPLC): an introduction", SEPARATION SCIENCE REDEFINED (2005).)

In certain embodiments, chromatographic resolution (e.g., HPLC) may be combined with mass spectrometry ("MS"). LC-MS methods are known in the art for oligonucleotide separation and identification using aqueous triethylammonium-hexafluoroisopropylalcohol (TEA HFIP) buffers compatible with MS detection (Apffel, A., et al., "New procedure for the use of HPLC-ESI MS for the analysis of nucleotides and oligonucleotides", J. CHROMATOGR. A, 777: 3-21 (1997)). Alternatively, a triethylammonium bicarbonate mobile phase may be used for oligonucleotide separation with postcolumn acetonitrile addition to the eluent. The ion-pairing buffer may be chosen to give the best MS detection sensitivity.

Quantitative analysis of capped fragment may also be performed using reverse phase-HPLC columns packed with 2.5 μm fully porous C18 sorbent, as described in Gilar, M., ANAL. BIOCHEM., 298: 196-206 (2001). Parameters that may be optimized to enhance oligonucleotide mass transfer in the stationary phase include elevated temperature, small sorbent particle size, and slow mobile phase flow rate. A triethylammonium acetate (TEAA) buffer with UV detection and an optimized TEA-HFIP mobile phase may be used for LC-MS separation and characterization of capped fragments.

In some embodiments, quantitation of capped fragments and the methylation status thereof, is achieved by automated integration of respective peak area in the HPLC chromatogram. Data may be presented as area percent value, which refers to the percentage of a particular species' integrated peak area relative to the total integrated peak area of the entire chromatograph.

In some embodiments, quantitation of capped and uncapped fragments may be achieved through other appropriate methods, for example, mass spectroscopy (MS)-based detection. It is contemplated that one of skill in the art may recognize additional applicable methods of quantitating capped and uncapped fragments as described herein.

Kits

The present invention further provides kits comprising various reagents and materials useful for carrying out inventive methods according to the present invention. The quantitative procedures described herein may be performed by diagnostic laboratories, experimental laboratories, or commercial laboratories. The invention provides kits which can be used in these different settings.

For example, materials and reagents for quantifying mRNA capping efficiency in an mRNA sample by enzymatic manipulation and chromatographic separation may be assembled together in a kit. In certain embodiments, an inventive kit comprises chromatographic columns and optionally agents for separating capped mRNA fragments on the column, and instructions for using the kit according to a method of the invention.

Each kit may preferably comprise the reagent which renders the procedure specific. Thus, for detecting/quantifying mRNA capping efficiency, kits may comprise a nucleic acid reagent of designed sequence that specifically anneals adjacent to an mRNA cap of a target. Kits may also comprise nucleases for production of the capped fragments; e.g., RNase H and/or S1 nuclease. Kits may further include in vitro transcription and capping reagents, enzymes and instructions for using the same.

Kits or other articles of manufacture according to the invention may include one or more containers to hold various reagents. Suitable containers include, for example, bottles, vials, syringes (e.g., pre-filled syringes), ampules. The container may be formed from a variety of materials such as glass or plastic.

In some embodiments, kits of the present invention may include suitable control levels or control samples for determining control levels as described herein. In some embodiments, kits of the invention may include instructions for using the kit according to one or more methods of the invention and may comprise instructions for in vitro transcription and capping.

EXAMPLES

Example 1: Synthesis of mRNA

Firefly Luciferase (FFL) and human erythropoietin (EPO) mRNA were synthesized by in vitro transcription from a plasmid DNA template encoding each respective gene. In vitro transcription included addition of a 5' cap structure, Cap1, which has a 2'-O-methyl residue at the 2' OH group of the ribose ring of base 1, by enzymatic conjugation of GTP via guanylyl transferase. A 3' poly(A) tail of approximately 200 nucleotides in length (as determined by gel electrophoresis) was incorporated through the addition of ATP in conjunction with PolyA polymerase (see detailed reaction conditions below). The in vitro transcription product included 5' and 3' untranslated regions, which are represented as X and Y, respectively, in the sequences below:

Human Erythropoietin (EPO) mRNA (SEQ ID NO: 1)

$X_1$AUGGGGGUGCACGAAUGUCCUGCCUGGCUGUGGCUUCUCCUGUCCCU

GCUGUCGCUCCCUCUGGGCCUCCCAGUCCUGGGCGCCCCACCACGCCUCA

UCUGUGACAGCCGAGUCCUGGAGAGGUACCUCUUGGAGGCCAAGGAGGC

CGAGAAUAUCACGACGGGCUGUGCUGAACACUGCAGCUUGAAUGAGAAU

```
AUCACUGUCCCAGACACCAAAGUUAAUUUCUAUGCCUGGAAGAGGAUGG

AGGUCGGGCAGCAGGCCGUAGAAGUCUGGCAGGGCCUGGCCCUGCUGUC

GGAAGCUGUCCUGCGGGGCCAGGCCCUGUUGGUCAACUCUUCCCAGCCG

UGGGAGCCCCUGCAGCUGCAUGUGGAUAAAGCCGUCAGUGGCCUUCGCA

GCCUCACCACUCUGCUUCGGGCUCUGGGAGCCCAGAAGGAAGCCAUCUC

CCCUCCAGAUGCGGCCUCAGCUGCUCCACUCCGAACAAUCACUGCUGAC

ACUUUCCGCAAACUCUUCCGAGUCUACUCCAAUUUCCUCCGGGGAAAGC

UGAAGCUGUACACAGGGGAGGCCUGCAGGACAGGGGACAGAUGAY₁
```

Codon-Optimized Firefly Luciferase (FFL) mRNA (SEQ ID NO: 2)

```
X₂AUGGAAGAUGCCAAAAACAUUAAGAAGGGCCCAGCGCCAUUCUACCC

ACUCGAAGACGGGACCGCCGGCGAGCAGCUGCACAAAGCCAUGAAGCGC

UACGCCCUGGUGCCCGGCACCAUCGCCUUUACCGACGCACAUAUCGAGG

UGGACAUUACCUACGCCGAGUACUUCGAGAUGAGCGUUCGGCUGGCAGA

AGCUAUGAAGCGCUAUGGGCUGAAUACAAACCAUCGGAUCGUGGUGUGC

AGCGAGAAUAGCUUGCAGUUCUUCAUGCCCGUGUUGGGUGCCCUGUUCA

UCGGUGUGGCUGUGGCCCCAGCUAACGACAUCUACAACGAGCGCGAGCU

GCUGAACAGCAUGGGCAUCAGCCAGCCCACCGUCGUAUUCGUGAGCAAG

AAAGGGCUGCAAAAGAUCCUCAACGUGCAAAAGAAGCUACCGAUCAUAC

AAAAGAUCAUCAUCAUGGAUAGCAAGACCGACUACCAGGGCUUCCAAAG

CAUGUACACCUUCGUGACUUCCCAUUUGCCACCCGGCUUCAACGAGUAC

GACUUCGUGCCCGAGAGCUUCGACCGGGACAAAACCAUCGCCCUGAUCA

UGAACAGUAGUGGCAGUACCGGAUUGCCCAAGGGCGUAGCCCUACCGCA

CCGCACCGCUUGUGUCCGAUUCAGUCAUGCCCGCGACCCCAUCUUCGGC

AACCAGAUCAUCCCCGACACCGCUAUCCUCAGCGUGGUGCCAUUUCACC

ACGGCUUCGGCAUGUUCACCACGCUGGGCUACUUGAUCUGCGGCUUUCG

GGUCGUGCUCAUGUACCGCUUCGAGGAGGAGCUAUUCUUGCGCAGCUUG

CAAGACUAUAAGAUUCAAUCUGCCCUGCUGGUGCCCACACUAUUUAGCU

UCUUCGCUAAGAGCACUCUCAUCGACAAGUACGACCUAAGCAACUUGCA

CGAGAUCGCCAGCGGCGGGGCGCCGCUCAGCAAGGAGGUAGGUGAGGCC

GUGGCCAAACGCUUCCACCUACCAGGCAUCCGCCAGGGCUACGGCCUGA

CAGAAACAACCAGCGCCAUUCUGAUCACCCCCGAAGGGGACGACAAGCC

UGGCGCAGUAGGCAAGGUGGUGCCCUUCUUCGAGGCUAAGGUGGUGGAC

UUGGACACCGGUAAGACACUGGGUGUGAACCAGCGCGGCGAGCUGUGCG

UCCGUGGCCCCAUGAUCAUGAGCGGCUACGUUAACAACCCCGAGGCUAC

AAACGCUCUCAUCGACAAGGACGGCUGGCUGCACAGCGGCGACAUCGCC

UACUGGGACGAGGACGAGCACUUCUUCAUCGUGGACCGGCUGAAGAGCC

UGAUCAAAUACAAGGGCUACCAGGUAGCCCCAGCCGAACUGGAGAGCAU

CCUGCUGCAACACCCCAACAUCUUCGACGCCGGGGUCGCCGGCCUGCCCG

ACGACGAUGCCGGCGAGCUGCCCGCCGCAGUCGUCGUGCUGGAACACGG
```

```
UAAAACCAUGACCGAGAAGGAGAUCGUGGACUAUGUGGCCAGCCAGGUU

ACAACCGCCAAGAAGCUGCGCGGUGGUGUUGUGUUCGUGGACGAGGUGC

CUAAAGGACUGACCGGCAAGUUGGACGCCCGCAAGAUCCGCGAGAUUCU

CAUUAAGGCCAAGAAGGGCGGCAAGAUCGCCGUGUAY₂
```

The 5' and 3' UTR sequences for X1/Y1 and X2/Y2 were as follows:

```
                                            (SEQ ID NO: 3)
X₁ = GGACAGAUCGCCUGGAGACGCCAUCCACGCUGUUUUGACCUCCA
UAGAAGACACCGGGACCGAUCCAGCCUCCGCGGCCGGGAACGGUGCAU
UGGAACGCGGAUUCCCCGUGCCAAGAGUGACUCACCGUCCUUGACACG (SEQ ID NO: 4)
X₂ = GGGAUCCUACC (SEQ ID NO: 5)
Y₁ = CGGGUGGCAUCCCUGUGACCCCUCCCCAGUGCCUCUCCUGGCCC
UGGAAGUUGCCACUCCAGUGCCCACCAGCCUUGUCCUAAUAAAAUUAA
GUUGCAUC (SEQ ID NO: 6)
Y₂ = UUUGAAUU
```

The synthesis of mRNA was conducted under complete RNAse-free conditions. All tubes, vials, pipette tips, pipettes, buffers, etc. were required nuclease-free. Messenger RNA was synthesized from a linearized DNA template. To produce the desired mRNA pre-cursor (IVT) construct, a mixture of ~100 ug of linearized DNA, rNTPs (3.33 mM), DTT (10 mM), T7 RNA polymerase, RNAse Inhibitor, Pyrophosphatase and reaction buffer (10×, 800 mM Hepes (pH8.0), 20 mM Spermidine, 250 mM MgCl₂, pH 7.7) was prepared with RNase-free water to a final volume of 2.24 ml. The reaction mixture was incubated at 37° C. for between 20-120 minutes. Upon completion, the mixture was treated with DNase I for an additional 15 minutes and quenched accordingly.

The purified mRNA product from the aforementioned IVT step was denatured at 65° C. for 10 minutes. Separately, portions of GTP (20 mM), S-adenosyl methionine, RNAse inhibitor, 2'-O-Methyltransferase and guanylyl transferase are mixed together with reaction buffer (10×, 500 mM Tris-HCl (pH 8.0), 60 mM KCl, 12.5 mM MgCl₂) to a final concentration of 8.3 ml. Upon denaturation, the mRNA was cooled on ice and then added to the reaction mixture. The combined solution was incubated at 37° C. for 20-90 minutes. Upon completion, aliquots of ATP (20 mM), PolyA Polymerase and tailing reaction buffer (10×, 500 mM Tris-HCl (pH 8.0), 2.5M NaCl, 100 mM MgCl₂) were added, and the total reaction mixture was further incubated at 37° C. for about 20-45 minutes. Upon completion, the final reaction mixture is quenched and purified accordingly.

Example 2: Chromatographic Quantification of Capping Efficiency

This example demonstrates chromatographic quantification of capping as well as methylation. Specifically, a twenty base DNA oligonucleotide is designed and synthesized to be complementary to the 5' UTR of an in vitro synthesized capped mRNA, specifically binding within one or two bases from the 5' cap, and preferably binding adjacent to the penultimate the mRNA (i.e., at the third nucleotide from the 5' end, the last two nucleotides of which are cap nucleotides. Binding of the DNA oligonucleotide to the 5' UTR adjacent to the cap establishes a well-defined region of DNA:RNA hybrid that is susceptible to RNAse H-mediated cleavage. In some embodiments, the DNA oligonucleotide is flanked on either end by 1-15 RNA nucleotides. In some embodiments, the DNA oligonucleotide is flanked on the 3' end by 1-15 RNA nucleotides.

RNAse H is added to a sample RNA solution comprising the hybridized in vitro synthesized mRNA. The RNAase H cleaves the in vitro synthesized capped mRNA in the region of the DNA:RNA hybrid, thereby producing a capped fragment. In certain embodiments, this cleavage is accomplished using an S1 Nuclease or other nuclease to create a blunt-end fragment marked at the 5' end by the cap analytes of choice. The fragment is preferably 2-10 nucleotides in length, including the cap nucleotides. Overall, this process provides a smaller molecule with increased resolution of both cap presence and cap modification.

After cleavage, the RNA solution is loaded onto a suitable chromatographic column for quantitative analysis of capped versus uncapped mRNA. In an exemplary embodiment, the column is an anion-exchange HPLC column, and the fragments are purified by adaptation of methods known to those of skill in the art (see, e.g., Wincott, F. et al, "Synthesis, deprotection, analysis and purification of RNA and ribozymes), NUCLEIC ACIDS RES 23: 2677-2684 (1995); Anderson, A. C., et al., "HPLC purification of RNA for crystallography and NMR", RNA, 2: 110-117, (1996)). The amount of capped fragments in the sample is determined by integrating chromatographic peaks corresponding to the capped and uncapped species. Data may be provided in the form of peak area or ratio of capped to uncapped peak area.

Figure 2:
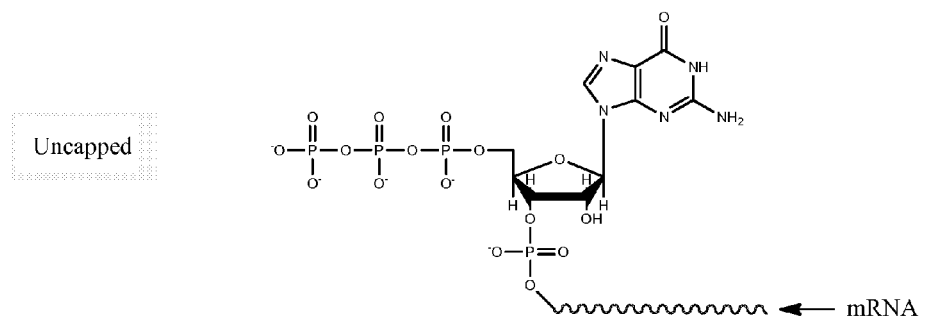
FIG. 2 is a diagram of exemplary mRNA capped structures and an uncapped structure present in various embodiments of the invention.
Figure 2:
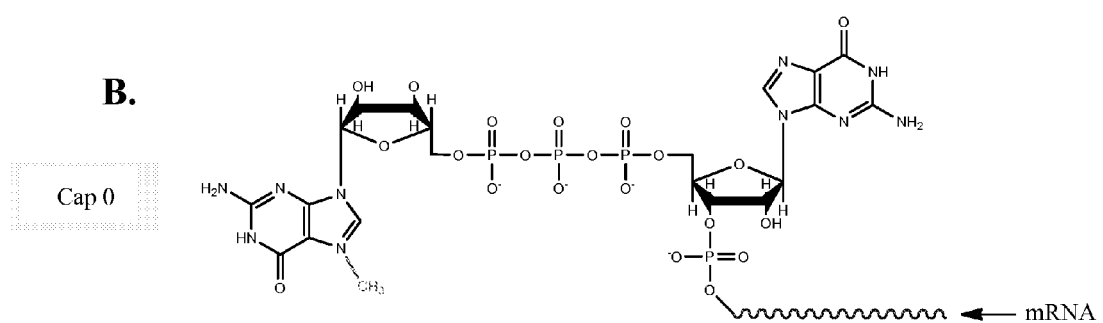
Figure 2:
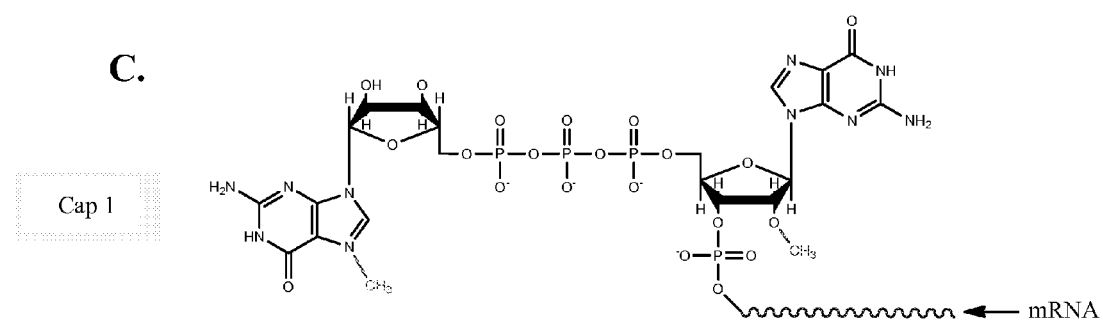

Concurrently, using the same method for analysis, the percent methylation of the guanine cap at the N-7 position is assessed. Even further, when synthesizing a "Cap 1" structure motif, one could separate species which are methylated at the 2'-O position of the ribose ring of the penultimate base (FIG. 2). Measurement of methylated nucleotides by HPLC may be achieved by a variety of methods, including methods incorporating electrochemical detection; see, e.g., Park and Ames (PROC. NATL. ACAD. SCI. USA, 85: 7467-7470 (1988)), incorporated by reference herein. This methodology provides a powerful combination of quantitative cap assessment as well as quantitative methylation assessment.

Example 3: Evaluation of mRNA 5' Capping on In Vivo Protein Production

In this example, we evaluated the impact of mRNA 5' capping on in vivo protein production and its potential impact on the efficacy of mRNA based therapy. Specifically, we evaluated the impact of 5' capping on the in vivo production of alpha-galactosidase A (alpha-Gal A), which is deficient in Fabry disease. Fabry disease is an X-linked inherited lysosomal storage disease characterized by severe renal impairment, angiokeratomas, and cardiovascular abnormalities, including ventricular enlargement and mitral valve insufficiency. Fabry disease also affects the peripheral nervous system, causing episodes of agonizing, burning pain in the extremities. Fabry disease is caused by a deficiency in the enzyme alpha-galactosidase A (alpha-Gal A). alpha-Gal A is the lysosomal glycohydrolase that cleaves the terminal alpha-galactosyl moieties of various glycoconjugates. Fabry disease results in a blockage of the catabolism of the neutral glycosphingolipid, ceramide trihexoside (CTH), and accumulation of this enzyme substrate within cells and in the bloodstream.

The cDNA and gene encoding human alpha-Gal A, GLA, have been isolated and sequenced. Human alpha-Gal A is expressed as a 429-amino acid polypeptide, of which the N-terminal 31 amino acids are the signal peptide. The human enzyme has been expressed in Chinese Hamster Ovary (CHO) cells (Desnick et al., U.S. Pat. No. 5,356,804; Ioannou et al., J. CELL BIOL., 119: 1137 (1992)); and insect cells (Calhoun et al., WO 90/11353).

Individuals suffering from Fabry disease may be treated by enzyme replacement therapy with human alpha-Gal A (see, e.g., U.S. Pat. No. 6,458,574, incorporated by reference herein). Additional approaches that modulate or supplement the expression of alpha-Gal A deficiency, and thus ameliorate the underlying deficiency, would be useful in the development of appropriate therapies for associated disorders. Such approaches include methods of intracellular delivery of nucleic acids (e.g., GLA mRNA) that are capable of correcting existing genetic defects and/or providing beneficial functions to one or more target cells. Following successful delivery to target tissues and cells, the compositions and nucleic acids transfect the target cell, and the nucleic acids (e.g., GLA mRNA) can be translated into the gene product of interest (e.g., alpha-GAL A) or can otherwise modulate/regulate the presence or expression of the gene product of interest. Such methods have been described previously; see, e.g. U.S. pre-grant publication 2011/0244026, incorporated by reference herein.

In this example, we evaluated the impact of the 5' capping on the in vivo protein production. Human GLA mRNA was synthesized by in vitro transcription from a plasmid DNA template encoding the gene, which was followed by the addition of a 5' cap structure, either Cap0 or Cap1 (Fechter, P. et al., J. GEN. VIROLOGY, 86: 1239-1249 (2005)). A 3' poly(A) tail of approximately 200 nucleotides in length as determined by gel electrophoresis was also added. The 5' and 3' untranslated regions present in the GLA mRNA are represented as X and Y in SEQ ID NO: 7, as indicated below:

Alpha-galactosidase (GLA) mRNA (SEQ ID NO: 7):

XAUGCAGCUGAGGAACCCAGAACUACAUCUGGGCUGCGCGCUUGCGCU

UCGCUUCCUGGCCCUCGUUUCCUGGGACAUCCCUGGGGCUAGAGCACU

GGACAAUGGAUUGGCAAGGACGCCUACCAUGGGCUGGCUGCACUGGGA

GCGCUUCAUGUGCAACCUUGACUGCCAGGAAGAGCCAGAUUCCUGCAU

CAGUGAGAAGCUCUUCAUGGAGAUGGCAGAGCUCAUGGUCUCAGAAGG

CUGGAAGGAUGCAGGUUAUGAGUACCUCUGCAUUGAUGACUGUUGGAU

GGCUCCCCAAAGAGAUUCAGAAGGCAGACUUCAGGCAGACCCUCAGCG

CUUUCCUCAUGGGAUUCGCCAGCUAGCUAAUUAUGUUCACAGCAAAGG

ACUGAAGCUAGGGAUUUAUGCAGAUGUUGGAAAUAAAACCUGCGCAGG

CUUCCCUGGGAGUUUGGAUACUACGACAUUGAUGCCCAGACCUUUGC

UGACUGGGGAGUAGAUCUGCUAAAAUUUGAUGGUUGUUACUGUGACAG

UUUGGAAAAUUUGGCAGAUGGUUAUAAGCACAUGUCCUUGGCCCUGAA

UAGGACUGGCAGAAGCAUUGUGUACUCCUGUGAGUGGCCUCUUUAUAU

GUGGCCCUUUCAAAAGCCCAAUUAUACAGAAAUCCGACAGUACUGCAA

UCACUGGCGAAAUUUUGCUGACAUUGAUGAUUCCUGGAAAAGUAUAAA

GAGUAUCUUGGACUGGACAUCUUUUAACCAGGAGAGAAUUGUUGAUGU

UGCUGGACCAGGGGGUUGGAAUGACCCAGAUAUGUUAGUGAUUGGCAA

CUUUGGCCUCAGCUGGAAUCAGCAAGUAACUCAGAUGGCCCUCUGGGC

UAUCAUGGCUGCUCCUUUAUUCAUGUCUAAUGACCUCCGACACAUCAG

CCCUCAAGCCAAAGCUCUCCUUCAGGAUAAGGACGUAAUUGCCAUCAA

UCAGGACCCCUUGGGCAAGCAAGGGUACCAGCUUAGACAGGGAGACAA

-continued
CUUUGAAGUGUGGGAACGACCUCUCUCAGGCUUAGCCUGGGCUGUAGC

UAUGAUAAACCGGCAGGAGAUUGGUGGACCUCGCUCUUAUACCAUCGC

AGUUGCUUCCCUGGGUAAAGGAGUGGCCUGUAAUCCUGCCUGCUUCAU

CACACAGCUCCUCCCUGUGAAAAGGAAGCUAGGGUUCUAUGAAUGGAC

UUCAAGGUUAAGAAGUCACAUAAAUCCCACAGGCACUGUUUUGCUUCA

GCUAGAAAAUACAAUGCAGAUGUCAUUAAAAGACUUACUUUAAY

X = GGGAUCCUACC
(SEQ ID NO: 4)

Y = UUUGAAUU
(SEQ ID NO: 6)

A codon-optimized alpha-galactosidase with PolyA insert (CO-GLA-PolyA) is also utilized in some embodiments (SEQ ID NO: 8):

X₁AUGCAGCUGAGGAACCCAGAGCUCCAUCUCGGAUGUGCACUGGCACU

UAGAUUCUCGCGCUUGUGUCGUGGGACAUCCCCGGAGCCAGGGCGCUG

GAUAAUGGGCUCGCCCGGACUCCCACAAUGGGUUGGCUGCACUGGGAGC

GCUUUAUGUGCAAUCUGGACUGCCAGGAAGAGCCCGAUAGCUGUAUUUC

GGAGAAGCUCUUCAUGGAAAUGGCGGAGUUGAUGGUGUCCGAAGGGUGG

AAGGAUGCGGGAUAUGAGUAUCUGUGUAUCGAUGACUGCUGGAUGGCAC

CGCAGCGAGAUUCGGAGGGGCGAUUGCAGGCCGACCCUCAGCGCUUCCC

UCAUGGAAUUCGGCAGCUGGCCAACUACGUACACUCAAAAGGACUUAAG

UUGGGGAUCUACGCGGACGUCGGUAAUAAGACAUGCGCUGGGUUCCCGG

GGAGCUUCGGAUACUAUGAUAUUGAUGCCCAGACCUUCGCGGACUGGGG

AGUGGACUUGCUUAAGUUUGAUGGUUGUUACUGUGACUCAUUGGAAAAC

UUGGCGGAUGGGUAUAAACAUAUGUCCUUGGCCUUGAAUCGGACAGGGC

GGUCGAUCGUCUACAGCUGCGAAUGGCCUUUGUAUAUGUGGCCGUUCCA

GAAACCCAACUACACCGAAAUUCGCCAGUAUUGCAAUCACUGGAGAAAC

UUCGCCGAUAUCGACGAUUCGUGGAAAUCAAUCAAGUCCAUCCUCGACU

GGACGUCCUUCAACCAAGAGAGAAUCGUAGAUGUGGCCGGACCGGGAGG

AUGGAACGACCCUGAUAUGCUUGUAAUUGGCAACUUUGGACUCUCGUGG

AACCAGCAAGUAACGCAAAUGGCACUCUGGGCUAUCAUGGCUGCGCCCC

UGUUCAUGUCAAACGACCUCAGGCACAUCUCGCCGCAGGCGAAAGCCUU

GCUUCAAGAUAAGGACGUCAUCGCGAUUAAUCAGGACCCGCUGGGGAAG

CAGGGCUAUCAGCUUAGACAGGGCGACAAUUUUGAGGUCUGGGAGCGAC

CCCUGAGCGACUCGCAUGGGCGGUGGCAAUGAUCAAUAGGCAGGAAAU

UGGUGGGCCGAGGUCGUACACUAUCGCCGUCGCGUCGUUGGGAAAGGGU

GUGGCGUGUAAUCCAGCGUGCUUUAUCACCCAACUGCUGCCCGUCAAGC

GCAAACUGGGUUUUUACGAAUGGACGAGCAGACUUCGCUCACACAUUAA

CCCAACGGGUACGGUGUUGCUCCAGCUCGAGAAUACAAUGCAAAUGUCA

CUUAAAGAUUUGCUCUGACGGGUGGCAUCCCUGUGACCCCUCCCCAGUG

CCUCUCCUGGCCCUGGAAGUUGCCACUCCAGUGCCCACCAGCCUUGCC

UAAUAAAAUUAAGUUGCAUCAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAA

The GLA mRNA was stored in water at a final concentration of 1 mg/mL at −80° C. until the time of use. All mRNA concentrations were determined via absorption (γmax 260 nm).

Suitable formulations for in vivo delivery of GLA Cap0 mRNA, GLA Cap1 mRNA, GLA mRNA and other controls include a multi-component lipid mixture of varying ratios employing one or more cationic lipids, helper lipids and PEGylated lipids. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids", J. CONTR. REL. 107: 276-287 (2005)), DLin-KC2-DMA (Semple, S. C. et al. "Rational Design of Cationic Lipids for siRNA Delivery", NATURE BIOTECH., 28: 172-176 (2010)), C12-200 (Love, K. T. et al. "Lipid-like materials for low-dose in vivo gene silencing", PROC NATL ACAD SCI., USA, 107: 1864-1869 (2010)), HGT4003, ICE, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of C6-C20 length. Lipid encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

Aliquots of 50 mg/mL ethanolic solutions of C12-200, DOPE, Chol and DMG-PEG2K were mixed and diluted with ethanol to 3 mL final volume. Separately, an aqueous buffered solution (10 mM citrate/150 mM NaCl, pH 4.5) of CO-GLA mRNA (Cap 0 or Cap 1) was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.72 mg/mL GLA mRNA (encapsulated). Zave=85.5 nm (Dv(50)=61.9 nm; Dv(90)=113 nm).

To determine whether the type of cap incorporated into GLA mRNA influenced protein production when the mRNA was encapsulated into C12-200-based lipid, an experiment was conducted in which wild type (CD-1) mice were injected with capped GLA mRNA species and subsequently monitored for human GLA protein production. The capped mRNA species included Cap0 (unmethylated at the 2'-O position) and Cap1(2'-O methylated)

The foregoing studies were performed using male CD-1 mice of approximately 6-8 weeks of age at the beginning of each experiment. Samples were introduced by a single bolus tail-vein injection of an equivalent total dose of 30 micrograms of encapsulated GLA, EPO, FIX or AIAT mRNA. Serum concentrations of GLA protein were determined at six hours. All animals were euthanized by $CO_2$ asphyxiation 6 hours post-dose administration (±5%) followed by thoracotomy and terminal cardiac blood collection. Whole blood (maximal obtainable volume) was collected via cardiac puncture on euthanized animals into serum separator tubes, allowed to clot at room temperature for at least 30 minutes, centrifuged at 22° C.±5° C. at 9300 g for 10 minutes, and the serum was extracted. For interim blood collection at six hours, approximately 40-50 µL of whole blood was be collected via facial vein puncture or tail snip. Samples collected from non-treatment animals were used as a baseline GLA levels for comparison to study animals. The liver and spleen of each mouse was harvested, apportioned into three parts and stored in either 10% neutral buffered formalin or snap-frozen and stored at 80° C.

Human GLA protein production was measured by enzyme-linked immunosorbent assay ("ELISA"). Standard ELISA procedures were followed employing sheep anti-Replagal G-188 IgG as the capture antibody with rabbit anti-Replagal IgG as the secondary (detection) antibody. Horseradish peroxidase (HRP)-conjugated goat anti-rabbit IgG was used for activation of the 3,3',5,5'-tetramethylbenzidine (TMB) substrate solution. The reaction was quenched using 2N $H_2SO_4$ after 20 minutes. Detection was monitored via absorption (450 nm) on a Molecular Device Flex Station instrument. Untreated mouse serum and human Replagal® protein were used as negative and positive controls, respectively.

Figure 3:
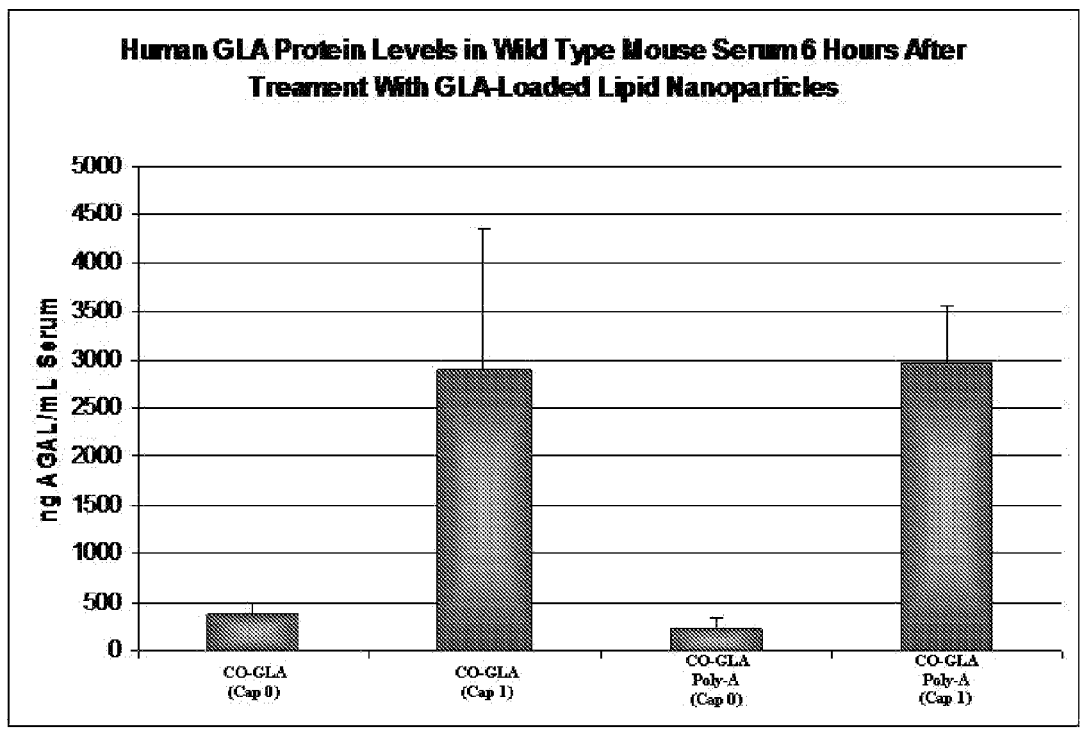
FIG. 3 is a bar graph demonstrating quantification of secreted human alpha-galactosidase (GLA) protein levels as measured via ELISA. The protein detected is a result of its production from GLA mRNA delivered intravenously via a single dose of lipid nanoparticles (30 ug encapsulated GLA mRNA) six hours post-administration.

As illustrated in FIG. 3, following the intravenous injection of capped species of CO-GLA mRNA loaded in the C12-200-based lipid nanoparticles, a substantial level of human GLA protein could be detected in mouse serum within 6 hours. Notably, there was a dramatic and statistically significant increase in protein production when employing mRNA with a Cap1 structure versus that of a Cap0 structure. These results demonstrated the importance of having the ability to characterize and quantify the capping and methylation efficiencies of the mRNA synthesis process.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a", "an" and "the" may mean one or more than one unless indicated to the contrary or otherwise evident from the context. Thus, for example, reference to "an antibody" includes a plurality of such antibodies, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are presenting, employed in, or otherwise relevant to a given product or process. Furthermore, it is to be understood that the invention encompasses all variations, combinations, and permutations in which one or more limitation, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for anyone of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understand of one of ordinary skill in the art, values that are expressed as ranges can assume any specific value or sub-range within the state ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

We claim:

1. A method of manufacturing mRNA having a quantified percentage of capped mRNA comprising the steps of:
   (1) manufacturing mRNA by in vitro synthesis to generate in vitro synthesized mRNA comprising capped mRNA and uncapped mRNA;
   (2) obtaining a sample of the in vitro synthesized mRNA;
   (3) annealing the mRNA sample with a DNA oligonucleotide complementary to a sequence in the 5' untranslated region of the in vitro synthesized mRNA, wherein the first base of the 3' end of the DNA oligonucleotide binds within 5 bases from the cap or uncapped penultimate base of mRNA under conditions that permit the DNA oligonucleotide to anneal to the sequence and form a DNA/RNA hybrid;
   (4) introducing to the sample one or more nucleases that selectively degrades the DNA/RNA hybrid, resulting in capped and uncapped fragments comprising no more than 5 bases of the mRNA;
   (5) separating the capped and uncapped fragments in the sample by chromatography and measuring the relative peak areas of the capped and uncapped fragments; and
   (6) determining the relative amount of the capped and uncapped fragments in the sample by determining the relative peak areas of the capped and uncapped fragments, thereby quantifying the percentage of capped mRNA.

2. The method of claim 1, further comprising a step of releasing the manufactured mRNA lot.

3. The method of claim 1, wherein the capped mRNA comprises a cap that has a structure of formula I:

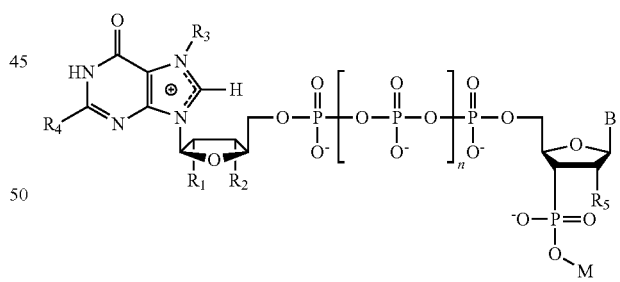

wherein,
B is a nucleobase;
$R_1$ is selected from a halogen, OH, and $OCH_3$;
$R_2$ is selected from H, OH, and $OCH_3$;
$R_3$ is $CH_3$, $CH_2CH_3$, $CH_2CH_2CH_3$ or void;
$R_4$ is $NH_2$;
$R_5$ is selected from OH, $OCH_3$ and a halogen;
n is 1, 2, or 3; and
M is a nucleotide of the mRNA.

4. The method of claim 3, wherein the nucleobase is guanine.

5. The method of claim 1, wherein the capped mRNA comprises a cap that is a $m^7G$ cap with a structure of formula II or an unmethylated cap with a structure of formula III:

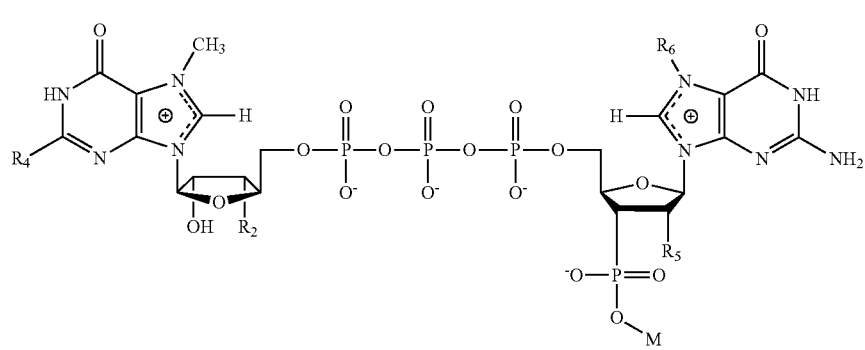

(II)

wherein,
$R_2$ is H or $CH_3$;
$R_4$ is $NH_2$;
$R_5$ is OH or $OCH_3$;
$R_6$ is H or $CH_3$, and
M is a nucleotide of the mRNA; or

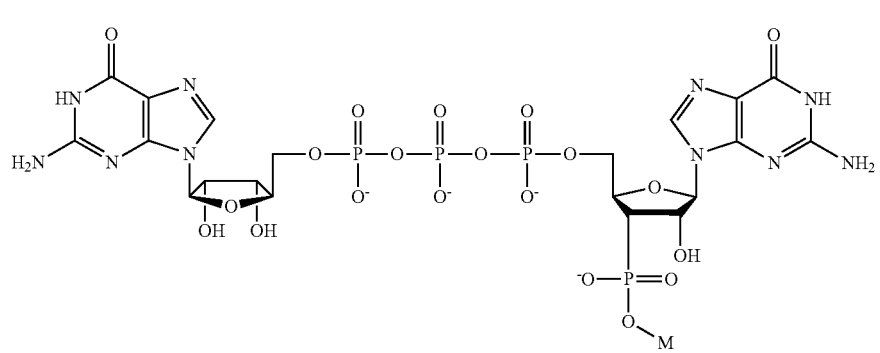

(III)

wherein M is a nucleotide of the mRNA.

6. The method of claim 1, wherein step (5) further separates methylated and unmethylated capped RNA.

7. The method of claim 6, wherein the methylated cap comprises methylation at $R_3$ and/or $R_5$ position.

8. The method of claim 6, wherein step (6) further comprises a step of quantitatively determining methylation percentage of the capped RNA.

9. The method of claim 1, wherein the DNA oligonucleotide is 10-80 nucleotides in length.

10. The method of claim 1, wherein the DNA oligonucleotide is linked to one or more RNA nucleotides.

11. The method of claim 1, wherein the one or more nucleases comprise RNase H.

12. The method of claim 1, wherein the one or more nucleases comprise a nuclease that generates blunt-ended capped and uncapped fragments.

13. The method of claim 12, wherein the nuclease is nuclease S1, RNAse H, or another 5' exonuclease.

14. The method of claim 1, wherein the capped and uncapped fragments comprise no more than 2 bases of the mRNA.

15. The method of claim 1, wherein the chromatography in step (5) is achieved with a chromatographic column selected from the group consisting of an anion-exchange HPLC column, a cation-exchange HPLC column, a reverse phase HPLC column, a hydrophobic interaction column, an ultra-performance liquid chromatography column, or a size exclusion column.

* * * * *

SEQUENCE LISTING

```
<160> NUMBER OF SEQ ID NOS: 8

<210> SEQ ID NO 1
<211> LENGTH: 822
<212> TYPE: RNA
<213> ORGANISM: Artificial Sequence
```

```
<220> FEATURE:
<223> OTHER INFORMATION: Description of Artificial Sequence: Synthetic
      polynucleotide

<400> SEQUENCE: 1
ggacagaucg ccuggagacg ccauccacgc uguuuugacc uccauagaag acaccgggac      60
cgauccagcc uccgcggccg ggaacggugc auuggaacgc ggauuccccg ugccaagagu     120
gacucaccgu ccuugacacg auggggguc acgaaugucc ugccggcug uggcuucucc      180 ugucccugcu gucgcucccu cugggccucc caguccuggg cgccccacca cgccucaucu     240
gugacagccg aguccuggag agguaccucu uggaggccaa ggaggccgag aauaucacga     300
cgggcugugc ugaacacugc agcuugaaug agaauaucac ugcccagac accaaaguua      360 auuucuaugc cuggaagagg auggaggucg ggcagcaggc cguagaaguc uggcagggcc     420
uggcccugcu gucggaagcu guccugcggg gccaggcccu guuggucaac ucuucccagc     480
cgugggagcc ccugcagcug caugggaua aagccgucag uggccuucgc agccucacca      540
cucugcuucg ggcucuggga gcccagaagg aagccaucuc cccuccagau gcggccucag     600
cugcuccacu ccgaacaauc acugcugaca cuuuccgcaa acucuuccga gucuaccuca     660
auuccuccgg gggaaagcug aagcuguaca caggggaggc cugcaggaca ggggacagau      720 gacgggguggc aucccuguga cccccucccca gugccucucc uggcccugga aguugccacu     780
ccagugccca ccagccuugu ccuaauaaaa uuaaguugca uc                         822

<210> SEQ ID NO 2
<211> LENGTH: 1671
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 2
gggauccuac cauggaagau gccaaaaaca uuaagaaggg cccagcgcca uucuacccac      60
ucgaagacgg gaccgccggc gagcagcugc acaaagccau gaagcgcuac gcccuggugc     120
ccggcaccau cgccuuuacc gacgcacaua ucgaggugga cauuaccuac gccgaguacu     180
ucgagaugag cguucggcug gcagaagcua ugaagcgcua ugggcugaau acaaaccauc     240
ggaucguggu gugcagcgag aauagcuugc aguucuucau gcccguguug ggugcccugu     300 ucaucgguu ggcugguggcc ccagcuaacg acaucuacaa cgagcgcgag cugcugaaca     360
gcaugggcau cagccagccc accgucguau ucgagcaa gaaagggcug caaaagaucc      420
ucaacgugca aaagaagcua ccgaucauac aaaagaucau caucauggau agcaagaccg     480
acuaccaggg cuuccaaagc auguacaccu ucgugacuuc ccauuugcca cccggcuuca     540
acgaguacga cuucgugccc gagagcuucg accgggacaa aaccaucgcc cugaucauga     600
acaguagugg caguaccgga uugcccaagg gcguagcccu accgcaccgc accgcuugug     660
uccgauucag ucaugcccgc gaccccaucu ucggcaacca gaucauccccc gacaccgcua     720 uccucagcgu ggugccauuu caccacggcu ucggcauguu caccacgcug gcuacuuga     780 ucugcggcuu cgggucgug cucaugauacc gcuucgagga ggagcuauuc uugcgcagcu     840
ugcaagacua uaagauucaa ucugcccugc uggugcccac acuauuuagc uucuucgcua     900
agagcacucu caucgacaag uacgaccuaa gcaacuugca cgagaucgcc agcggcgggg     960
cgccgcucag caaggaggua ggugaggccg uggccaaacg cuuccaccua ccaggcaucc    1020
```

-continued

| | |
|---|---|
| gccagggcua cggccugaca gaaacaacca gcgccauucu gaucaccccc gaagggacg | 1080 |
| acaagccugg cgcaguaggc aaggugguge ccuucuucga ggcuaaggug guggacuugg | 1140 |
| acaccgguaa gacacugggu gugaaccagc gcggcgagcu gugcguccgu ggccccauga | 1200 |
| ucaugagcgg cuacguuaac aaccccgagg cuacaaacgc ucucaucgac aaggacggcu | 1260 |
| ggcugcacag cggcgacauc gccuacuggg acgaggacga gcacuucuuc aucguggacc | 1320 |
| ggcugaagag ccugaucaaa uacaagggcu accagguagc cccagccgaa cuggagagca | 1380 |
| uccugcugca acaccccaac aucuucgacg ccggggucgc cggccugccc gacgacgaug | 1440 |
| ccggcgagcu gcccgccgca gucgucgugc uggaacacgg uaaaaccaug accgagaagg | 1500 |
| agaucgugga cuauguggcc agccagguua caaccgccaa gaagcugcgc gguggguuug | 1560 |
| uguucgugga cgaggugccu aaaggacuga ccggcaaguu ggacgcccgc aagauccgcg | 1620 |
| agauucucau uaaggccaag aagggcggca agaucgccgu guauugaau u | 1671 |

<210> SEQ ID NO 3
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| ggacagaucg ccuggagacg ccauccacgc uguuugacc uccauagaag acaccgggac | 60 |
| cgauccagcc uccgcggccg ggaacggugc auuggaacgc ggauucccg ugccaagagu | 120 |
| gacucaccgu ccuugacacg | 140 |

<210> SEQ ID NO 4
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4

| | |
|---|---|
| gggauccuac c | 11 |

<210> SEQ ID NO 5
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---|
| cggguggcau cccugugacc ccuccccagu gccucuccug gcccuggaag uugccacucc | 60 |
| agugcccacc agccuugucc uaauaaaauu aaguugcauc | 100 |

<210> SEQ ID NO 6
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

| | |
|---|---|
| uuugaauu | 8 |

<210> SEQ ID NO 7
<211> LENGTH: 1309
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7

```
gggauccuac caugcagcug aggaacccag aacuacaucu gggcugcgcg cuugcgcuuc     60
gcuuccuggc ccucguuucc ugggacaucc cuggggcuag agcacuggac aauggauugg    120
caaggacgcc uaccaugggc uggcugcacu gggagcgcuu caugugcaac cuugacugcc    180
aggaagagcc agauuccugc aucagugaga agcucuucau ggagauggca gagcucaugg    240
ucucagaagg cuggaaggau gcagguuaug aguaccucug cauugaugac uguuggaugg    300
cuccccaaag agauucagaa ggcagacuuc aggcagaccc ucagcgcuuu ccucauggga    360
uucgccagcu agcuaauuau guucacagca aaggacugaa gcuagggauu uaugcagaug    420
uuggaaauaa aaccugcgca ggcuucccug ggaguuuugg auacuacgac auugaugccc    480
agaccuuugc ugacgggga guagaucugc uaaaauuuga ugguuguuac ugugacaguu    540
uggaaaauuu ggcagauggu uauaagcaca uguccuuggc ccugaauagg acuggcagaa    600
gcauugugua cuccgugag uggcucuuu auauguggcc cuuucaaaag cccaauuaua    660
cagaaauccg acaguacugc aaucacuggc gaaauuugc ugacauugau gauccugga    720 aaaguauaaa gaguaucuug gacuggacau cuuuuaacca ggagagaauu guugaugug    780 cuggaccagg ggguuggaau gacccagaua uguuagugau uggcaacuuu ggccucagcu    840
ggaaucagca aguaacucag auggcccucu gggcuaucau ggcugcuccu uuauucaugu    900
cuaaugaccu ccgacacauc agcccucaag ccaaagcucu ccuucaggau aaggacguaa    960
uugccaucaa ucaggacccc uugggcaagc aagggucacca gcuugacag ggagacaacu   1020 uugaagugug gaacgaccu cucucaggcu uagccugggc uguagcuaug auaaaccggc   1080
aggagauugg uggaccucgc ucuuauacca ucgcaguugc uucccuggu aaaggagugg   1140 ccuguaaucc ugccugcuuc aucacacagc uccucccugu gaaaaggaag cuagggnucu   1200
augaauggac uucaagguua agaagucaca uaaaucccac aggcacuguu uugcuucagc   1260 uagaaauac aaugcagaug ucauuaaaag acuuacuuua auuugaauu                1309
```

<210> SEQ ID NO 8
<211> LENGTH: 1650
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8

```
ggacagaucg ccuggagacg ccauccacgc uguuuugacc uccauagaag acaccgggac     60
cgauccagcc uccgcggccg ggaacggugc auuggaacgc ggauucccg ugccaagagu    120 gacucaccgu ccuugacacg augcagcuga ggaacccaga gcccaucuc ggaugugcac    180 uggcacuuag auuucucgcg cuuuguucgu gggacauccc cggagccagg gcgcuggaua    240 auggcucgc ccgacucccc acaauggguu ggcugcacug ggagcgcuuu augugcaauc    300
uggacugcca ggaagagccc gauagcugua uuucggagaa gcucuucaug gaauggcgg    360
```

-continued

```
aguugauggu guccgaaggg uggaaggaug cgggauauga guaucugugu aucgaugacu      420
gcuggauggc accgcagcga gauucggagg ggcgauugca ggccgacccu cagcgcuucc      480
cucauggaau ucggcagcug gccaacuacg uacacucaaa aggacuuaag uuggggaucu      540
acgcggacgu cgguaauaag acaugcgcug gguucccggg gagcuucgga uacuaugaua      600
uugaugccca gaccuucgcg gacuggggag uggacuugcu uaaguuugau gguuguuacu      660
gugacucauu ggaaaacuug gcggaugggu auaaacauau guccuuggcc uugaaucgga      720
cagggcgguc gaucgucuac agcugcgaau ggccuuugua uauguggccg uuccagaaac      780
ccaacuacac cgaaauucgc caguauugca aucacuggag aaacuucgcc gauaucgacg      840
auucguggaa aucaaucaag uccauccucg acuggacguc cuucaaccaa gagagaaucg      900
uagaugugcg cggaccggga ggauggaacg acccugauau gcuuguaauu ggcaacuuug      960
gacucucgug gaaccagcaa guaacgcaaa uggcacucug ggcuaucaug gcugcgcccc     1020
uguucauguc aaacgaccuc aggcacaucu cgccgcaggc gaaagccuug cuucaagaua     1080
aggacgucau cgcgauuaau caggacccgc uggggaagca gggcuaucag cuuagacagg     1140
gcgacaauuu ugaggucugg gagcgacccc ugagcggacu cgcaugggcg guggcaauga     1200
ucaauaggca ggaaauuggu gggccgaggu cguacacuau cgccgucgcg ucguugggaa     1260
agggugugcc guguaaucca gcgugcuuua ucacccaacu gcugcccguc aagcgcaaac     1320 ugggcuuuuua cgaauggacg agcagacuuc gcucacacau uaacccaacg gguacggugu     1380
ugcuccagcu cgagaauaca augcaaaugu cacuuaaaga uuugcucuga cggguggcau     1440 cccgugacc ccuccccagu gccucuccug gcccuggaag uugccacucc agugcccacc     1500
agccuugucc uaauaaaauu aaguugcauc aaaaaaaaaa aaaaaaaaaa aaaaaaaaaa     1560
aaaaaaaaaa aaaaaaaaaa aaaaaaaaaa aaaaaaaaaa aaaaaaaaaa aaaaaaaaaa     1620
aaaaaaaaaa aaaaaaaaaa aaaaaaaaaa                                     1650
```